United States Patent
Witham et al.

(10) Patent No.: US 11,793,891 B2
(45) Date of Patent: Oct. 24, 2023

(54) FLUORESCEIN FORMULATIONS AND KITS

(71) Applicant: OPUS LIFE SCIENCES LLC, Corvallis, OR (US)

(72) Inventors: Patrick H. Witham, Eugene, OR (US); William Stringer, St. Petersburg, FL (US)

(73) Assignee: OPUS LIFE SCIENCES, LLC, Corvallis, OR (US)

( * ) Notice: Subject to any disclaimer, the term of this patent is extended or adjusted under 35 U.S.C. 154(b) by 0 days.

(21) Appl. No.: 18/118,723

(22) Filed: Mar. 7, 2023

(65) Prior Publication Data

US 2023/0277693 A1    Sep. 7, 2023

Related U.S. Application Data

(60) Provisional application No. 63/317,529, filed on Mar. 7, 2022.

(51) Int. Cl.
*A61K 49/00* (2006.01)
*A61J 1/14* (2023.01)
*B65D 1/02* (2006.01)
*B65D 81/24* (2006.01)

(52) U.S. Cl.
CPC ......... *A61K 49/0043* (2013.01); *A61J 1/1468* (2015.05); *A61K 49/0071* (2013.01); *B65D 1/023* (2013.01); *B65D 1/0207* (2013.01); *B65D 1/0261* (2013.01); *B65D 81/24* (2013.01)

(58) Field of Classification Search
CPC .. A61K 49/0043; B65D 1/0207; B65D 1/023; B65D 1/0261; C03C 17/003–005
USPC ............................................. 428/34.1–36.92
See application file for complete search history.

(56) References Cited

U.S. PATENT DOCUMENTS

| | | | |
|---|---|---|---|
| 6,944,493 B2* | 9/2005 | Alam | A61K 49/0034 600/431 |
| 10,293,047 B1* | 5/2019 | Witham | A61K 47/02 |
| 10,632,197 B2* | 4/2020 | Witham | A61K 47/10 |
| 10,842,872 B2* | 11/2020 | Witham | A61K 49/0043 |
| 11,452,779 B2* | 9/2022 | Witham | A61K 31/245 |
| 2007/0218007 A1* | 9/2007 | Chang | A61K 9/107 424/9.6 |
| 2008/0176930 A1* | 7/2008 | Bydlinski | C07D 311/82 549/392 |
| 2014/0251859 A1* | 9/2014 | Weikart | A61L 31/08 206/524.9 |
| 2014/0371569 A1* | 12/2014 | Caruso | A61K 49/006 600/405 |
| 2015/0021339 A1* | 1/2015 | Felts | C23C 16/401 220/626 |

(Continued)

OTHER PUBLICATIONS https://www.accessdata.fda.gov/drugsatfda_docs/label/2006/021980s000lbl.pdf (Year: 2023).*

(Continued)

*Primary Examiner* — Michael C Romanowski
(74) *Attorney, Agent, or Firm* — Procopio, Cory, Hargreaves & Savitch LLP

(57) ABSTRACT

Compositions comprising a fluorescein component and benoxinate component and the corresponding uses of these compositions are described herein. These compositions have improved storage life and the fluorescein component and/or benoxinate component minimally degrade after 12 to 18 months of storage.

23 Claims, 12 Drawing Sheets

(56) References Cited

U.S. PATENT DOCUMENTS

2018/0249943 A1* 9/2018 Moein .................... A61B 10/04
2018/0280239 A1* 10/2018 Miyazaki ................. A61J 1/05

OTHER PUBLICATIONS https://www.acs.org/molecule-of-the-week/archive/f/fluorescein.html (Year: 2013).*

* cited by examiner

Roughening Reaction zone Delaminated area (left) and reaction zone (right)

| Element (mg/L) | Citrate buffer (pH 6.0) | Sodium bicarbonate (about pH 8.0) | Phosphate buffer (pH 7.0) |
|---|---|---|---|
| B | 2.1 | 2.0 | 1.1 |
| Al | 3.0 | 0.05 | 0.06 |
| Si | 20.1 | 8.2 | 9.2 |

SEM-micrographs of sample set 01, vial 2 (RLD vial).

SEM-micrograph of sample set 01, vial 5 (RLD vial)

SEM-micrograph of sample set 02, vial 4 (empty control vial)

SEM-micrograph of sample set 03, vial 3 (t0: initial).

SEM-micrograph of sample set 03, vial 7 (t0: initial).

SEM-micrographs of sample set 04, vial 9 (Fortis vials, t1: 5 weeks, 60 °C).

SEM-micrograph of sample set 04, vial 10 (Fortis vials, t1: 5 weeks, 60 °C).

FLUORESCEIN FORMULATIONS AND KITS

BACKGROUND OF THE DISCLOSURE

Fluorescein is a dye that is widely used as a diagnostic tool in the medical field. Fluorescein sodium, the sodium salt of fluorescein, is used in ophthalmology and optometry for the diagnosis of corneal abrasions, corneal ulcers and herpetic corneal infections, and other ophthalmic diseases and conditions.

Intravenous or oral fluorescein is used in fluorescein angiography or angioscopy in diagnosis of vascular disorders including retinal disease macular degeneration, diabetic retinopathy, inflammatory intraocular conditions, and intraocular tumors. It is also being used increasingly during surgery for brain tumors. Diluted fluorescein dye has been used to localise multiple muscular ventricular septal defects during open heart surgery and confirm the presence of any residual defects.

Fluorescein sodium is approved by the FDA for diagnostic fluorescein angiography or angioscopy of the retina and iris vasculature.

SUMMARY OF THE DISCLOSURE

Provided in one aspect is a kit, comprising: an aqueous formulation comprising from about 50 mg/mL to about 300 mg/mL fluorescein sodium, wherein the formulation has a pH of from about 8 to about 10; and a glass vial holding the aqueous formulation, wherein the aqueous formulation has a dissolved silicon concentration upon filling the glass vial ($Si_{0w}$), and a dissolved silicon concentration after storage in the glass vial at 60° C. for 10 weeks ($Si_{10w}$), wherein $Si_{10w}/Si_{0w}$ is from 1 to 1.6.

In some embodiments, $Si_{10w}/Si_{0w}$ is from 1 to 1.5. In some embodiments, $Si_{10w}/Si_{0w}$ is from 1 to 1.4. In some embodiments, $Si_{10w}/Si_{0w}$ is from 1 to 1.3. In some embodiments, $Si_{10w}/Si_{0w}$ is from 1 to 1.25. In some embodiments, $Si_{10w}/Si_{0w}$ is from 1 to 1.22.

In some embodiments, $Si_{10w}$ is less than 14 mg/L. In some embodiments, $Si_{10w}$ is less than 13.5 mg/L. In some embodiments, $Si_{10w}$ is less than 13 mg/L. In some embodiments, $Si_{10w}$ is less than 12.5 mg/L. In some embodiments, $Si_{10w}$ is less than 12 mg/L. In some embodiments, $Si_{10w}$ is less than 11.5 mg/L.

Provided in another aspect is a kit, comprising: an aqueous formulation comprising from about 50 mg/mL to about 300 mg/mL fluorescein sodium, wherein the formulation has a pH of from about 8 to about 10; and a glass vial holding the aqueous formulation, wherein the aqueous formulation has a dissolved boron concentration upon filling the glass vial ($B_{0w}$), and a dissolved boron concentration after storage in the glass vial at 60° C. for 10 weeks ($B_{10w}$), wherein $B_{10w}/B_{0w}$ is from 1 to 1.9.

In some embodiments, $B_{10w}/B_{0w}$ is from 1 to 1.8. In some embodiments, $B_{10w}/B_{0w}$ is from 1 to 1.7. In some embodiments, $B_{10w}/B_{0w}$ is from 1 to 1.6. In some embodiments, $B_{10w}/B_{0w}$ is from 1 to 1.5. In some embodiments, $B_{10w}/B_{0w}$ is from 1 to 1.4. In some embodiments, $B_{10w}/B_{0w}$ is from 1 to 1.3.

In some embodiments, $B_{10w}$ is less than 2.2 mg/L. In some embodiments, $B_{10w}$ is less than 2.1 mg/L. In some embodiments, $B_{10w}$ is less than 2.0 mg/L. In some embodiments, $B_{10w}$ is less than 1.9 mg/L. In some embodiments, $B_{10w}$ is less than 1.85 mg/L.

Provided in another aspect is a kit, comprising: an aqueous formulation comprising from about 50 mg/mL to about 300 mg/mL fluorescein sodium, wherein the formulation has a pH of from about 8 to about 10; and a glass vial holding the aqueous formulation, wherein the aqueous formulation has a dissolved silicon concentration upon filling the glass vial ($Si_{0w}$), and a dissolved silicon concentration after storage in the glass vial at 60° C. for 10 weeks ($Si_{10w}$), wherein $Si_{10w}/Si_{0w}$ is from 1 to 1.6, and wherein the aqueous formulation has a dissolved boron concentration upon filling the glass vial ($B_{0w}$), and a dissolved boron concentration after storage in the glass vial at 60° C. for 10 weeks ($B_{10w}$), wherein $B_{10w}/B_{0w}$ is from 1 to 1.9.

In some embodiments, $Si_{10w}/Si_{0w}$ is from 1 to 1.5. In some embodiments, $Si_{10w}/Si_{0w}$ is from 1 to 1.4. In some embodiments, $Si_{10w}/Si_{0w}$ is from 1 to 1.3. In some embodiments, $Si_{10w}/Si_{0w}$ is from 1 to 1.25. In some embodiments, $Si_{10w}/Si_{0w}$ is from 1 to 1.22. In some embodiments, $Si_{10w}$ is less than 14 mg/L. In some embodiments, $Si_{10w}$ is less than 13.5 mg/L. In some embodiments, $Si_{10w}$ is less than 13 mg/L. In some embodiments, $Si_{10w}$ is less than 12.5 mg/L. In some embodiments, $Si_{10w}$ is less than 12 mg/L. In some embodiments, $Si_{10w}$ is less than 11.5 mg/L.

In some embodiments, $B_{10w}/B_{0w}$ is from 1 to 1.8. In some embodiments, $B_{10w}/B_{0w}$ is from 1 to 1.7. In some embodiments, $B_{10w}/B_{0w}$ is from 1 to 1.6. In some embodiments, $B_{10w}/B_{0w}$ is from 1 to 1.5. In some embodiments, $B_{10w}/B_{0w}$ is from 1 to 1.4. In some embodiments, $B_{10w}/B_{0w}$ is from 1 to 1.3. In some embodiments, $B_{10w}$ is less than 2.2 mg/L. In some embodiments, $B_{10w}$ is less than 2.1 mg/L. In some embodiments, $B_{10w}$ is less than 2.0 mg/L. In some embodiments, $B_{10w}$ is less than 1.9 mg/L. In some embodiments, $B_{10w}$ is less than 1.85 mg/L.

Provided in another aspect is a kit, comprising: an aqueous formulation comprising from about 50 mg/mL to about 300 mg/mL fluorescein sodium, wherein the formulation has a pH of from about 8 to about 10; and a glass vial holding the aqueous formulation, wherein the glass vial has a bottom reaction zone upon filling the glass vial ($BTRZ_{0w}$) of no more than 20 nm, and the glass vial has a bottom reaction zone after storage in the glass vial at 60° C. for 10 weeks ($BTRZ_{10w}$) of no more than 250 nm.

In some embodiments, $BTRZ_{10w}$ is no more than 200 nm. In some embodiments, $BTRZ_{10w}$ is no more than 180 nm. In some embodiments, $BTRZ_{10w}$ is no more than 160 nm. In some embodiments, $BTRZ_{10w}$ is no more than 150 nm. In some embodiments, $BTRZ_{10w}$ is no more than 140 nm. In some embodiments, $BTRZ_{10w}$ is no more than 130 nm. In some embodiments, $BTRZ_{10w}$ is no more than 100 nm. In some embodiments, $BTRZ_{10w}$ is no more than 50 nm. In some embodiments, $BTRZ_{10w}$ is no more than 40 nm. In some embodiments, $BTRZ_{10w}$ is no more than 30 nm. In some embodiments, $BTRZ_{10w}$ is no more than 20 nm. In some embodiments, $BTRZ_{10w}$ is no more than 10 nm.

In some embodiments, $BTRZ_{0w}$ is no more than 30 nm. In some embodiments, $BTRZ_{0w}$ is no more than 20 nm. In some embodiments, $BTRZ_{0w}$ is no more than 10 nm.

In some embodiments, in addition to the reaction zone features, the aqueous formulation has a dissolved silicon concentration upon filling the glass vial ($Si_{0w}$), and a dissolved silicon concentration after storage in the glass vial at 60° C. for 10 weeks ($Si_{10w}$), wherein $Si_{10w}/Si_{0w}$ is from 1 to 1.6.

In some embodiments, $Si_{10w}/Si_{0w}$ is from 1 to 1.5. In some embodiments, $Si_{10w}/Si_{0w}$ is from 1 to 1.4. In some embodiments, $Si_{10w}/Si_{0w}$ is from 1 to 1.3. In some embodiments, $Si_{10w}/Si_{0w}$ is from 1 to 1.25. In some embodiments, $Si_{10w}/Si_{0w}$ is from 1 to 1.22. In some embodiments, $Si_{10w}$ is less than 14 mg/L. In some embodiments, $Si_{10w}$ is less than 13.5 mg/L. In some embodiments, $Si_{10w}$ is less than 13 mg/L. In some embodiments, $Si_{10w}$ is less than 12.5 mg/L. In some embodiments, $Si_{10w}$ is less than 12 mg/L. In some embodiments, $Si_{10w}$ is less than 11.5 mg/L.

In some embodiments, in addition to the reaction zone features, the aqueous formulation has a dissolved boron concentration upon filling the glass vial ($B_{0w}$), and a dissolved boron concentration after storage in the glass vial at 60° C. for 10 weeks ($B_{10w}$), wherein $B_{10w}/B_{0w}$ is from 1 to 1.9.

In some embodiments, $B_{10w}/B_{0w}$ is from 1 to 1.8. In some embodiments, $B_{10w}/B_{0w}$ is from 1 to 1.7. In some embodiments, $B_{10w}/B_{0w}$ is from 1 to 1.6. In some embodiments, $B_{10w}/B_{0w}$ is from 1 to 1.5. In some embodiments, $B_{10w}/B_{0w}$ is from 1 to 1.4. In some embodiments, $B_{10w}/B_{0w}$ is from 1 to 1.3. In some embodiments, $B_{10w}$ is less than 2.2 mg/L. In some embodiments, $B_{10w}$ is less than 2.1 mg/L. In some embodiments, $B_{10w}$ is less than 2.0 mg/L. In some embodiments, $B_{10w}$ is less than 1.9 mg/L. In some embodiments, $B_{10w}$ is less than 1.85 mg/L.

In some embodiments, the aqueous formulation comprising from about 70 mg/mL to about 130 mg/mL of fluorescein sodium. In some embodiments, the aqueous formulation comprising from about 90 mg/mL to about 110 mg/mL of fluorescein sodium. In some embodiments, the aqueous formulation comprising about 100 mg/mL of fluorescein sodium.

In some embodiments, the aqueous formulation comprising from about 200 mg/mL to about 300 mg/mL of fluorescein sodium. In some embodiments, the aqueous formulation comprising from about 230 mg/mL to about 270 mg/mL of fluorescein sodium. In some embodiments, the aqueous formulation comprising about 250 mg/mL of fluorescein sodium.

In some embodiments, the aqueous formulation has a pH of from about 8.0 to about 9.8. In some embodiments, the aqueous formulation comprises at least one pH adjusting agent. In some embodiments, the at least one pH adjusting agent comprises sodium hydroxide, hydrochloric acid, or a combination thereof. In some embodiments, the aqueous formulation is a solution.

In some embodiments, the glass vial is sealed. In some embodiments, the glass vial has a fill volume of from 2 mL to 5 mL. In some embodiments, the glass vial has a fill volume of 5 mL. In some embodiments, the glass vial has a fill volume of 2 mL.

In some embodiments, the glass vial is a Schott DC vial. In some embodiments, the glass vial is made from Fiolax glass and comprises a strengthened shoulder to reduce delamination.

In some embodiments, the glass vial has a shoulder reaction zone upon filling the glass vial ($SHRZ_{0w}$) of no more than 20 nm, and the glass vial has a shoulder reaction zone after storage in the glass vial at 60° C. for 10 weeks ($SH_{10w}$) of no more than 250 nm.

In some embodiments, the glass vial has a shoulder reaction zone upon filling the glass vial ($SHRZ_{0w}$) of no more than 20 nm, and the glass vial has a shoulder reaction zone after storage in the glass vial at 60° C. for 10 weeks ($SH_{10w}$) of no more than 200 nm.

In some embodiments, the glass vial has a shoulder reaction zone upon filling the glass vial ($SHRZ_{0w}$) of no more than 20 nm, and the glass vial has a shoulder reaction zone after storage in the glass vial at 60° C. for 10 weeks ($SH_{10w}$) of no more than 190 nm.

In some embodiments, the glass vial has a shoulder reaction zone upon filling the glass vial ($SHRZ_{0w}$) of no more than 20 nm, and the glass vial has a shoulder reaction zone after storage in the glass vial at 60° C. for 10 weeks ($SH_{10w}$) of no more than 180 nm.

In some embodiments, the glass vial has a shoulder reaction zone upon filling the glass vial ($SHRZ_{0w}$) of no more than 20 nm, and the glass vial has a shoulder reaction zone after storage in the glass vial at 60° C. for 10 weeks ($SH_{10w}$) of no more than 170 nm.

In some embodiments, the glass vial has a shoulder reaction zone upon filling the glass vial ($SHRZ_{0w}$) of no more than 20 nm, and the glass vial has a shoulder reaction zone after storage in the glass vial at 60° C. for 10 weeks ($SH_{10w}$) of no more than 160 nm.

In some embodiments, the glass vial has a shoulder reaction zone upon filling the glass vial ($SHRZ_{0w}$) of no more than 20 nm, and the glass vial has a shoulder reaction zone after storage in the glass vial at 60° C. for 10 weeks ($SH_{10w}$) of no more than 150 nm.

In some embodiments, the glass vial has a shoulder reaction zone upon filling the glass vial ($SHRZ_{0w}$) of no more than 20 nm, and the glass vial has a shoulder reaction zone after storage in the glass vial at 60° C. for 10 weeks ($SH_{10w}$) of no more than 140 nm.

In some embodiments, the glass vial has a shoulder reaction zone upon filling the glass vial ($SHRZ_{0w}$) of no more than 20 nm, and the glass vial has a shoulder reaction zone after storage in the glass vial at 60° C. for 10 weeks ($SH_{10w}$) of no more than 100 nm.

In some embodiments, the glass vial has a shoulder reaction zone upon filling the glass vial ($SHRZ_{0w}$) of no more than 20 nm, and the glass vial 80 nm.

In some embodiments, the glass vial has a shoulder reaction zone upon filling the glass vial ($SHRZ_{0w}$) of no more than 20 nm, and the glass vial has a shoulder reaction zone after storage in the glass vial at 60° C. for 10 weeks ($SH_{10w}$) of no more than 60 nm.

In some embodiments, the glass vial has a shoulder reaction zone upon filling the glass vial ($SHRZ_{0w}$) of no more than 20 nm, and the glass vial has a shoulder reaction zone after storage in the glass vial at 60° C. for 10 weeks ($SH_{10w}$) of no more than 50 nm.

In some embodiments, the glass vial comprises a neck portion having a cylindrical neck wall, a body portion having a cylindrical body wall, and a shoulder portion having a frustoconical shoulder wall that interconnects the neck and body portions, wherein the shoulder wall that extends toward the cylindrical body wall at a transition angle ($\beta$) of at least 120°.

In some embodiments, the frustoconical shoulder wall extends toward the cylindrical body wall at a transition angle ($\beta$) of between 120°-170°. In some embodiments, the frustoconical shoulder wall extends toward the cylindrical body wall at a transition angle ($\beta$) of between 120°-130°. In some embodiments, the frustoconical shoulder wall extends toward the cylindrical body wall at a transition angle ($\beta$) of between 130°-140°. In some embodiments, the frustoconical shoulder wall extends toward the cylindrical body wall at a transition angle ($\beta$) of between 140°-150°. In some embodiments, the frustoconical shoulder wall extends toward the cylindrical body wall at a transition angle ($\beta$) of between 150°-160°. In some embodiments, the frustoconical shoulder wall extends toward the cylindrical body wall at a transition angle ($\beta$) of between 160°-170°.

In some embodiments, the frustoconical shoulder wall extends toward the cylindrical neck wall at a transition angle ($\alpha$) of at least 120°. In some embodiments, the frustoconical shoulder wall extends toward the cylindrical neck wall at a transition angle (α) of between 120°-170°. In some embodiments, the frustoconical shoulder wall extends toward the cylindrical neck wall at a transition angle (α) of between 120°-130°. In some embodiments, the frustoconical shoulder wall extends toward the cylindrical neck wall at a transition angle (α) of between 130°-140°. In some embodiments, the frustoconical shoulder wall extends toward the cylindrical neck wall at a transition angle (α) of between 140°-150°. In some embodiments, the frustoconical shoulder wall extends toward the cylindrical neck wall at a transition angle (α) of between 150°-160°. In some embodiments, the frustoconical shoulder wall extends toward the cylindrical neck wall at a transition angle (α) of between 160°-170°.

In some embodiments, the formulation is suitable for injection. In some embodiments, the formulation is suitable for intravenous injection. In some embodiments, the kit is used in diagnosis of an ophthalmic disease or condition. In some embodiments, the kit is used in fluorescein angiography.

BRIEF DESCRIPTION OF DRAWINGS

The objects and features of the present can be better understood with reference to the following detailed description and accompanying drawings.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE DISCLOSURE

Provided herein are kits for fluorescein or fluorescein sodium that have reduced amount of delamination or glass attack on the vial, and/or the resulting delaminated glass impurities in the formulation. In some embodiment, the kit has reduced amount of delamination or glass attack on the vial, and/or the resulting delaminated glass impurities in the formulation after storage conditions, e.g. 10 weeks of storage at about 60° C.

Fluorescein

Fluorescein is a disclosing agent. Fluorescein sodium is the sodium salt of fluorescein and has a molecular formula of $C_{20}H_{10}Na_2O_5$, molecular weight of 376.28, and the following chemical structure:

The chemical name for fluorescein sodium is spiro [isobenzofuran-1(3H), 9'-[9H]xanthene]-3-one, 3'6'-dihydroxy, disodium salt.

In some embodiments, the fluorescein component of the compositions described herein is fluorescein or the pharmaceutically acceptable salt thereof. In some embodiments, the pharmaceutically acceptable salt of fluorescein is the sodium salt.

Fluorescein Formulations

In some embodiments, the aqueous formulation comprising from about 70 mg/mL to about 130 mg/mL of fluorescein. In some embodiments, the aqueous formulation comprising from about 90 mg/mL to about 110 mg/mL of fluorescein. In some embodiments, the aqueous formulation comprising about 100 mg/mL of fluorescein.

In some embodiments, the aqueous formulation comprising from about 200 mg/mL to about 300 mg/mL of fluorescein. In some embodiments, the aqueous formulation comprising from about 230 mg/mL to about 270 mg/mL of fluorescein. In some embodiments, the aqueous formulation comprising about 250 mg/mL of fluorescein.

In some embodiments, the aqueous formulation has a pH of from about 8.0 to about 9.8. In some embodiments, the aqueous formulation comprises at least one pH adjusting agent. In some embodiments, the at least one pH adjusting agent comprises sodium hydroxide, hydrochloric acid, or a combination thereof. In some embodiments, the aqueous formulation is a solution.

Glass Vials

In some embodiments, the glass vial is sealed. In some embodiments, the glass vial has a fill volume of from 2 mL to 5 mL. In some embodiments, the glass vial has a fill volume of 5 mL. In some embodiments, the glass vial has a fill volume of 2 mL.

Conventional Vial

Figure 1:
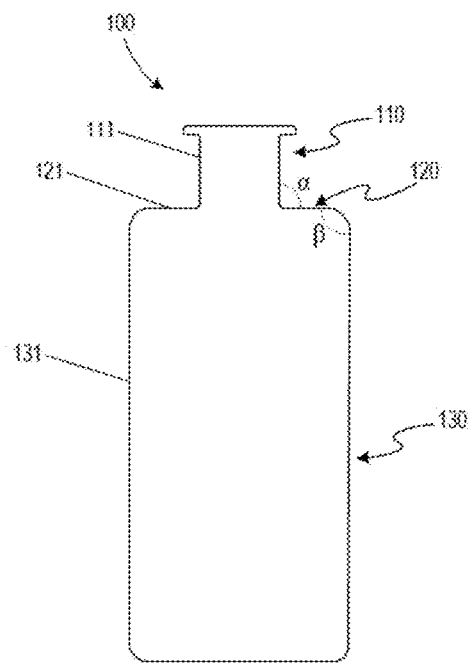
FIG. 1 illustrates a conventional vial, and shows the shoulder-body transition angle (β) and the shoulder-neck transition angle (α) of the vial.
Figure 2:
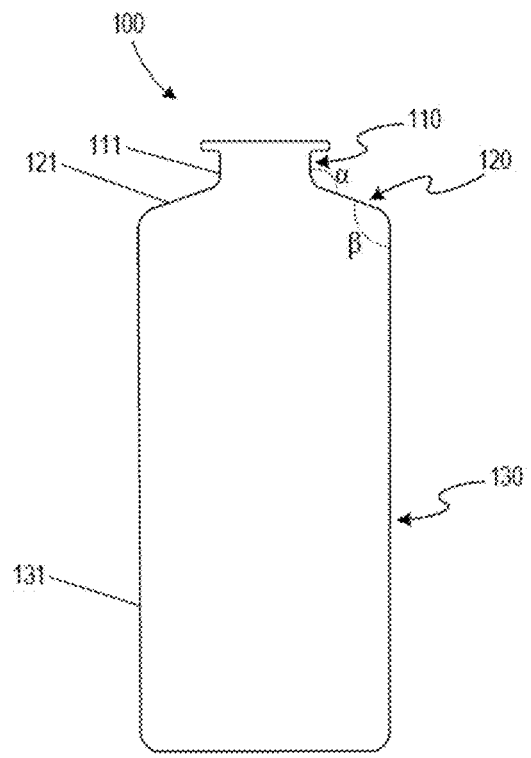
FIG. 2 illustrates another conventional vial, and shows the shoulder-body transition angle (β) and the shoulder-neck transition angle (α) of the vial.

Referring to FIGS. 1-2, two conventional vials (100) for injectable products are illustrated as having a neck portion (110) including a cylindrical neck wall (111) and a body portion (130) including a cylindrical body wall (131). The cylindrical body wall (131) has a diameter large than a diameter of the cylindrical neck wall (111). The vials further include a shoulder portion (120) that interconnects the neck and body portions (110, 130). The shoulder portion (120) includes a frustoconical shoulder wall (121) that extends toward the cylindrical body wall (131) at a transition angle (β) of less than 120°. The frustoconical shoulder wall (121) also extends toward the cylindrical neck wall (111) at a transition angle (α) of less than 120°.

As illustrated in FIG. 1, the shoulder-body transition angle (β) of the conventional vial is close to 90°; and the shoulder-neck transition angle (α) of the conventional vial is also close to 90°. As illustrated in FIG. 2, the shoulder-body transition angle (β) of the conventional vial is close to 110°; and the shoulder-neck transition angle (α) of the conventional vial is also close to 110°.

Improved Vials—General

Figure 3:
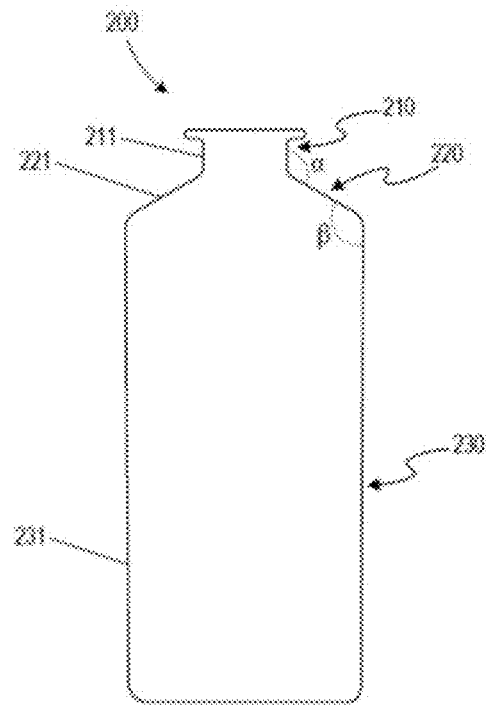
FIG. 3 illustrates one embodiment of a vial according to the present disclosure, and shows the shoulder-body transition angle (β) and the shoulder-neck transition angle (α) of the vial.
Figure 4:
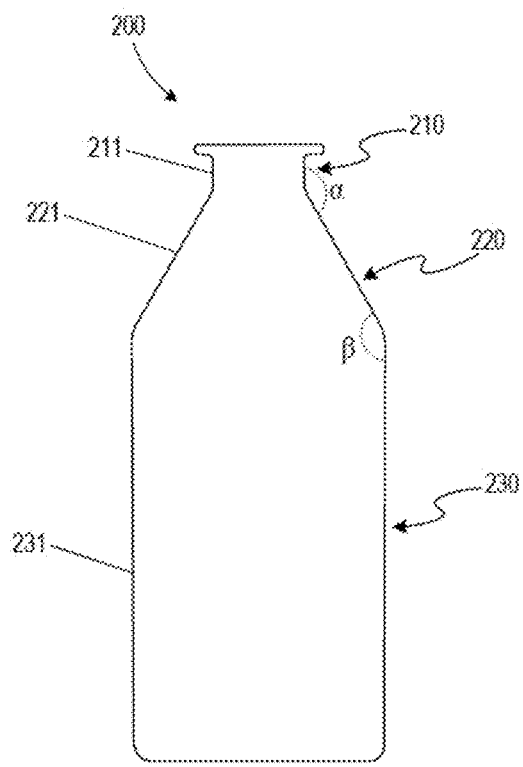
FIG. 4 illustrates another embodiment of a vial according to the present disclosure, and shows the shoulder-body transition angle (β) and the shoulder-neck transition angle (α) of the vial.
Figure 5:
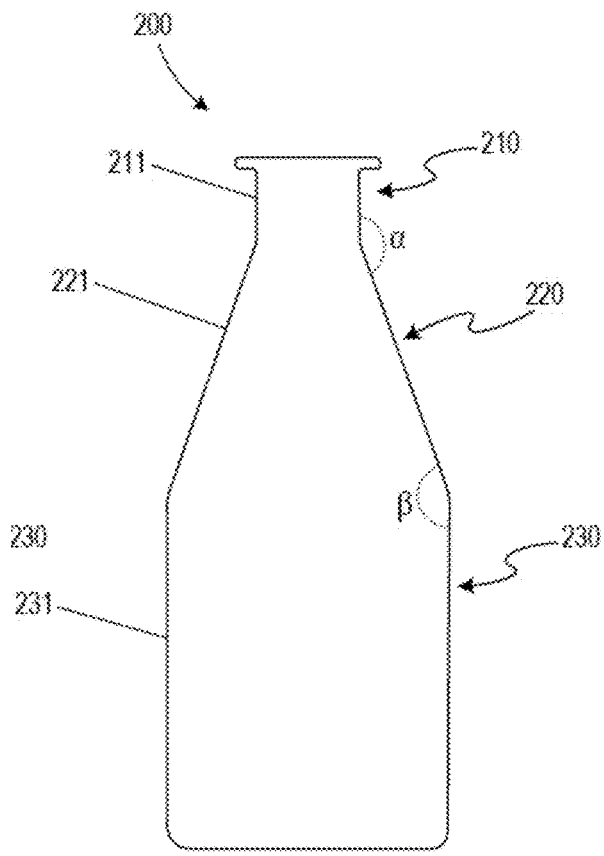
FIG. 5 illustrates another embodiment of a vial according to the present disclosure, and shows the shoulder-body transition angle (β) and the shoulder-neck transition angle (α) of the vial.

Referring to FIGS. 3-5, improved vials according to certain aspect of the present disclosure are illustrated as having a neck portion including a cylindrical neck wall and a body portion including a cylindrical body wall. The cylindrical body wall has a diameter large than a diameter of the cylindrical neck wall. The improved bottle further includes a shoulder portion that interconnects the neck and body portions. The shoulder portion includes a frustoconical shoulder wall that extends toward the cylindrical body wall at a transition angle (β) of at least 120°. The frustoconical shoulder wall also extends toward the cylindrical neck wall at a transition angle (α) of at least 120°.

Improved Vials—Shoulder-Body Transition Angle (β)

In some embodiments, the frustoconical shoulder wall extends toward the cylindrical body wall at a transition angle of between 120°-170°. In some embodiments, the frustoconical shoulder wall extends toward the cylindrical body wall at a transition angle of between 125°-170°. In some embodiments, the frustoconical shoulder wall extends toward the cylindrical body wall at a transition angle of between 130°-170°. In some embodiments, the frustoconical shoulder wall extends toward the cylindrical body wall at a transition angle of between 135°-170°. In some embodiments, the frustoconical shoulder wall extends toward the cylindrical body wall at a transition angle of between 140°-170°. In some embodiments, the frustoconical shoulder wall extends toward the cylindrical body wall at a transition angle of between 150°-170°. In some embodiments, the frustoconical shoulder wall extends toward the cylindrical body wall at a transition angle of between 160°-170° (e.g. FIG. 5).

In some embodiments, the frustoconical shoulder wall extends toward the cylindrical body wall at a transition angle of between 120°-160°. In some embodiments, the frustoconical shoulder wall extends toward the cylindrical body wall at a transition angle of between 125°-160°. In some embodiments, the frustoconical shoulder wall extends toward the cylindrical body wall at a transition angle of between 130°-160°. In some embodiments, the frustoconical shoulder wall extends toward the cylindrical body wall at a transition angle of between 135°-160°. In some embodiments, the frustoconical shoulder wall extends toward the cylindrical body wall at a transition angle of between 140°-160°. In some embodiments, the frustoconical shoulder wall extends toward the cylindrical body wall at a transition angle of between 150°-160° (e.g. FIG. 4).

In some embodiments, the frustoconical shoulder wall extends toward the cylindrical body wall at a transition angle of between 120°-150°. In some embodiments, the frustoconical shoulder wall extends toward the cylindrical body wall at a transition angle of between 125°-150°. In some embodiments, the frustoconical shoulder wall extends toward the cylindrical body wall at a transition angle of between 130°-150°. In some embodiments, the frustoconical shoulder wall extends toward the cylindrical body wall at a transition angle of between 135°-150°. In some embodiments, the frustoconical shoulder wall extends toward the cylindrical ne body ck wall at a transition angle of between 140°-150°.

In some embodiments, the frustoconical shoulder wall extends toward the cylindrical body wall at a transition angle of between 120°-140°. In some embodiments, the frustoconical shoulder wall extends toward the cylindrical body wall at a transition angle of between 125°-140°. In some embodiments, the frustoconical shoulder wall extends toward the cylindrical body wall at a transition angle of between 130°-140°. In some embodiments, the frustoconical shoulder wall extends toward the cylindrical body wall at a transition angle of between 135°-140° (e.g. FIG. 3).

Improved Vials—Shoulder-Neck Transition Angle (α)

In some embodiments, the frustoconical shoulder wall extends toward the cylindrical neck wall at a transition angle of between 120°-170°. In some embodiments, the frustoconical shoulder wall extends toward the cylindrical neck wall at a transition angle of between 125°-170°. In some embodiments, the frustoconical shoulder wall extends toward the cylindrical neck wall at a transition angle of between 130°-170°. In some embodiments, the frustoconical shoulder wall extends toward the cylindrical neck wall at a transition angle of between 135°-170°. In some embodiments, the frustoconical shoulder wall extends toward the cylindrical neck wall at a transition angle of between 140°-170°. In some embodiments, the frustoconical shoulder wall extends toward the cylindrical neck wall at a transition angle of between 150°-170°. In some embodiments, the frustoconical shoulder wall extends toward the cylindrical neck wall at a transition angle of between 160°-170° (e.g. FIG. 5).

In some embodiments, the frustoconical shoulder wall extends toward the cylindrical neck wall at a transition angle of between 120°-160°. In some embodiments, the frustoconical shoulder wall extends toward the cylindrical neck wall at a transition angle of between 125°-160°. In some embodiments, the frustoconical shoulder wall extends toward the cylindrical neck wall at a transition angle of between 130°-160°. In some embodiments, the frustoconical shoulder wall extends toward the cylindrical neck wall at a transition angle of between 135°-160°. In some embodiments, the frustoconical shoulder wall extends toward the cylindrical neck wall at a transition angle of between 140°-160°. In some embodiments, the frustoconical shoulder wall extends toward the cylindrical neck wall at a transition angle of between 150°-160° (e.g. FIG. 4).

In some embodiments, the frustoconical shoulder wall extends toward the cylindrical neck wall at a transition angle of between 120°-150°. In some embodiments, the frustoconical shoulder wall extends toward the cylindrical neck wall at a transition angle of between 125°-150°. In some embodiments, the frustoconical shoulder wall extends toward the cylindrical neck wall at a transition angle of between 130°-150°. In some embodiments, the frustoconical shoulder wall extends toward the cylindrical neck wall at a transition angle of between 135°-150°. In some embodiments, the frustoconical shoulder wall extends toward the cylindrical neck wall at a transition angle of between 140°-150°.

In some embodiments, the frustoconical shoulder wall extends toward the cylindrical neck wall at a transition angle of between 120°-140°. In some embodiments, the frustoconical shoulder wall extends toward the cylindrical neck wall at a transition angle of between 125°-140°. In some embodiments, the frustoconical shoulder wall extends toward the cylindrical neck wall at a transition angle of between 130°-140° (e.g. FIG. 3). In some embodiments, the frustoconical shoulder wall extends toward the cylindrical neck wall at a transition angle of between 135°-140°.

In some embodiments, the glass vial is a Schott DC vial. In some embodiments, the glass vial is made from Fiolax glass and comprises a strengthened shoulder to reduce delamination.

Glass Delamination/Contamination

Glass vials used for injectable products generally come in two manufacturing formats—molded or tubular. Molded vials are less common and more expensive. The manufacturer molds the vial in one piece by pouring liquid glass into a mold. Tubular vials are manufactured by cutting glass tubes, then forming the tube into the desired shape using heat in an automated process called converting. It is generally believed that molded vials are more resistant to delamination.

There is also a variant of tubular vials called Delamination Control (DC) where the heating/forming/converting process is fine tuned to reduce the likelihood of delamination, such as by removing debris of glass attached to the tube caused by the cutting process. Additionally, the tubes can be made with special glass to reduce delamination.

Example 3 shows key protocols and parameters for glass delamination studies, some of which are used in the present disclosure.

Glass Delamination/Contamination in Fluorescein Product Kits

The present disclosure recognizes that glass vials that contain fluorescein or fluorescein sodium formulations have delamination or glass attack on the vial during storage, which can result in delaminated, dissociated, and/or dissolved glass impurities in the formulations before the formulations are used, for example through intravenous injection.

Referring to Example 4, which includes a delamination/contamination study of 10% fluorescein sodium product kit currently on the market (RLD; 5 mL molded glass vials). Example 4 also includes a study of 10% fluorescein sodium in modified vials that are converted from tubular glass from Schott (Fortis; 5 mL tubular glass vials). Unexpectedly, the RLD product exhibited evidence of delamination at time 0 (i.e. upon filling with the 10% fluorescein sodium bulk solution). Also, the Fortis vial unexpectedly showed early evidence of delamination after 5 weeks storage at 60° C.

Referring now to Example 5, which includes a delamination/contamination study of 10% fluorescein sodium in three glass vials—(1) Piramal molded vial, (2) Schott tubular vial, and (3) Schott tubular DC vial. While the DC vial performed better than the other two vials, all three showed evidence of glass attack and early indicators of delamination after only 2.5 weeks at 60° C.

Fluorescein Product Kits with Improved Glass Delamination/Contamination

Referencing now to Example 6, which includes a delamination/contamination study of 10% fluorescein sodium in improved glass vials. In this non-limiting example, the improved glass vial is made with Fiolax glass and has a strengthened shoulder to make it more delamination-resistant. Without wishing to be bound by any particular theory, it is contemplated that while the formulation in the glass vial may not reach the shoulder area of the vial throughout the storage time period, a strengthened shoulder would contribute to reduce the delamination/contamination of the vial during storage, an insight heretofore unknown. As shown in Example 6 and summarized below, evidence of delamination was only observed after 10 weeks at 60° C. indicating the improved vial with strengthened shoulder performed better than the commercial fluorescein product kits and conventional glass vials, including those designed to resist delamination (e.g. Schott's DC vials).

Silicon in Formulation

In some embodiments, the aqueous formulation has a dissolved silicon concentration upon filling the glass vial ($Si_{0w}$), and a dissolved silicon concentration after storage in the glass vial at 60° C. for 10 weeks ($Si_{10w}$), wherein $Si_{10w}/Si_{0w}$ is from 1 to 1.6.

In some embodiments, $Si_{10w}/Si_{0w}$ is from 1 to 1.5. In some embodiments, $Si_{10w}/Si_{0w}$ is from 1 to 1.4. In some embodiments, $Si_{10w}/Si_{0w}$ is from 1 to 1.3. In some embodiments, $Si_{10w}/Si_{0w}$ is from 1 to 1.25. In some embodiments, $Si_{10w}/Si_{0w}$ is from 1 to 1.22.

In some embodiments, $Si_{10w}/Si_{0w}$ is $Si_{10w}$ is less than 14 mg/L. In some embodiments, $Si_{10w}/Si_{0w}$ is $Si_{10w}$ is less than 13.5 mg/L. In some embodiments, $Si_{10w}/Si_{0w}$ is $Si_{10w}$ is less than 13 mg/L. In some embodiments, $Si_{10w}/Si_{0w}$ is $Si_{10w}$ is less than 12.5 mg/L. In some embodiments, $Si_{10w}/Si_{0w}$ is $Si_{10w}$ is less than 12 mg/L. In some embodiments, $Si_{10w}/Si_{0w}$ is $Si_{10w}$ is less than 11.5 mg/L.

Boron in Formulation

In some embodiments, the aqueous formulation has a dissolved boron concentration upon filling the glass vial ($B_{0w}$), and a dissolved boron concentration after storage in the glass vial at 60° C. for 10 weeks ($B_{10w}$), wherein $Si_{10w}/Si_{0w}$ is from 1 to 1.9.

In some embodiments, $B_{10w}/B_{0w}$ is from 1 to 1.8. In some embodiments, $B_{10w}/B_{0w}$ is from 1 to 1.7. In some embodiments, $B_{10w}/B_{0w}$ is from 1 to 1.6. In some embodiments, $B_{10w}/B_{0w}$ is from 1 to 1.5. In some embodiments, $B_{10w}/B_{0w}$ is from 1 to 1.4. In some embodiments, $B_{10w}/B_{0w}$ is from 1 to 1.3.

In some embodiments, $B_{10w}$ is less than 2.2 mg/L. In some embodiments, $B_{10w}$ is less than 2.1 mg/L. In some embodiments, $B_{10w}$ is less than 2.0 mg/L. In some embodiments, $B_{10w}$ is less than 1.9 mg/L. In some embodiments, $B_{10w}$ is less than 1.85 mg/L.

Silicon and Boron in Formulation

In some embodiments, the aqueous formulation has a dissolved silicon concentration upon filling the glass vial ($Si_{0w}$), and a dissolved silicon concentration after storage in the glass vial at 60° C. for 10 weeks ($Si_{10w}$), wherein $Si_{10w}/Si_{0w}$ is from 1 to 1.6; and the aqueous formulation has a dissolved boron concentration upon filling the glass vial ($B_{0w}$), and a dissolved boron concentration after storage in the glass vial at 60° C. for 10 weeks ($B_{10w}$), wherein $Si_{10w}/Si_{0w}$ is from 1 to 1.9.

In some embodiments, $Si_{10w}/Si_{0w}$ is from 1 to 1.5. In some embodiments, $Si_{10w}/Si_{0w}$ is from 1 to 1.4. In some embodiments, $Si_{10w}/Si_{0w}$ is from 1 to 1.3. In some embodiments, $Si_{10w}/Si_{0w}$ is from 1 to 1.25. In some embodiments, $Si_{10w}/Si_{0w}$ is from 1 to 1.22. In some embodiments, $Si_{10w}/Si_{0w}$ is $Si_{10w}$ is less than 14 mg/L. In some embodiments, $Si_{10w}/Si_{0w}$ is $Si_{10w}$ is less than 13.5 mg/L. In some embodiments, $Si_{10w}/Si_{0w}$ is $Si_{10w}$ is less than 13 mg/L. In some embodiments, $Si_{10w}/Si_{0w}$ is $Si_{10w}$ is less than 12.5 mg/L. In some embodiments, $Si_{10w}/Si_{0w}$ is $Si_{10w}$ is less than 12 mg/L. In some embodiments, $Si_{10w}/Si_{0w}$ is $Si_{10w}$ is less than 11.5 mg/L.

In some embodiments, $B_{10w}/B_{0w}$ is from 1 to 1.8. In some embodiments, $B_{10w}/B_{0w}$ is from 1 to 1.7. In some embodiments, $B_{10w}/B_{0w}$ is from 1 to 1.6. In some embodiments, $B_{10w}/B_{0w}$ is from 1 to 1.5. In some embodiments, $B_{10w}/B_{0w}$ is from 1 to 1.4. In some embodiments, $B_{10w}/B_{0w}$ is from 1 to 1.3. In some embodiments, $B_{10w}$ is less than 2.2 mg/L. In some embodiments, $B_{10w}$ is less than 2.1 mg/L. In some embodiments, $B_{10w}$ is less than 2.0 mg/L. In some embodiments, $B_{10w}$ is less than 1.9 mg/L. In some embodiments, $B_{10w}$ is less than 1.85 mg/L.

Bottom Reaction Zone

In some embodiments, the glass vial has a bottom reaction zone upon filling the glass vial ($BTRZ_{0w}$) of no more than 20 nm, and the glass vial has a bottom reaction zone after storage in the glass vial at 60° C. for 10 weeks ($BTRZ_{10w}$) of no more than 250 nm.

In some embodiments, $BTRZ_{10w}$ is no more than 200 nm. In some embodiments, $BTRZ_{10w}$ is no more than 180 nm. In some embodiments, $BTRZ_{10w}$ is no more than 160 nm. In some embodiments, $BTRZ_{10w}$ is no more than 150 nm. In some embodiments, $BTRZ_{10w}$ is no more than 140 nm. In some embodiments, $BTRZ_{10w}$ is no more than 130 nm. In some embodiments, $BTRZ_{10w}$ is no more than 100 nm. In some embodiments, $BTRZ_{10w}$ is no more than 50 nm. In some embodiments, $BTRZ_{10w}$ is no more than 40 nm. In some embodiments, $BTRZ_{10w}$ is no more than 30 nm. In some embodiments, $BTRZ_{10w}$ is no more than 20 nm. In some embodiments, $BTRZ_{10w}$ is no more than 10 nm.

In some embodiments, $BTRZ_{0w}$ is no more than 30 nm. In some embodiments, $BTRZ_{0w}$ is no more than 20 nm. In some embodiments, $BTRZ_{0w}$ is no more than 10 nm.

Shoulder Reaction Zone

In some embodiments, the glass vial has a shoulder reaction zone upon filling the glass vial ($SHRZ_{0w}$) of no more than 20 nm, and the glass vial has a shoulder reaction zone after storage in the glass vial at 60° C. for 10 weeks ($SH_{10w}$) of no more than 250 nm.

In some embodiments, the glass vial has a shoulder reaction zone upon filling the glass vial ($SHRZ_{0w}$) of no more than 20 nm, and the glass vial has a shoulder reaction zone after storage in the glass vial at 60° C. for 10 weeks ($SH_{10w}$) of no more than 200 nm.

In some embodiments, the glass vial has a shoulder reaction zone upon filling the glass vial ($SHRZ_{0w}$) of no more than 20 nm, and the glass vial has a shoulder reaction zone after storage in the glass vial at 60° C. for 10 weeks ($SH_{10w}$) of no more than 190 nm.

In some embodiments, the glass vial has a shoulder reaction zone upon filling the glass vial ($SHRZ_{0w}$) of no more than 20 nm, and the glass vial has a shoulder reaction zone after storage in the glass vial at 60° C. for 10 weeks ($SH_{10w}$) of no more than 180 nm.

In some embodiments, the glass vial has a shoulder reaction zone upon filling the glass vial ($SHRZ_{0w}$) of no more than 20 nm, and the glass vial has a shoulder reaction zone after storage in the glass vial at 60° C. for 10 weeks ($SH_{10w}$) of no more than 170 nm.

In some embodiments, the glass vial has a shoulder reaction zone upon filling the glass vial ($SHRZ_{0w}$) of no more than 20 nm, and the glass vial has a shoulder reaction zone after storage in the glass vial at 60° C. for 10 weeks ($SH_{10w}$) of no more than 160 nm.

In some embodiments, the glass vial has a shoulder reaction zone upon filling the glass vial ($SHRZ_{0w}$) of no more than 20 nm, and the glass vial has a shoulder reaction zone after storage in the glass vial at 60° C. for 10 weeks ($SH_{10w}$) of no more than 150 nm.

In some embodiments, the glass vial has a shoulder reaction zone upon filling the glass vial ($SHRZ_{0w}$) of no more than 20 nm, and the glass vial has a shoulder reaction zone after storage in the glass vial at 60° C. for 10 weeks ($SH_{10w}$) of no more than 140 nm.

In some embodiments, the glass vial has a shoulder reaction zone upon filling the glass vial ($SHRZ_{0w}$) of no more than 20 nm, and the glass vial has a shoulder reaction zone after storage in the glass vial at 60° C. for 10 weeks ($SH_{10w}$) of no more than 100 nm.

In some embodiments, the glass vial has a shoulder reaction zone upon filling the glass vial ($SHRZ_{0w}$) of no more than 20 nm, and the glass vial 80 nm.

In some embodiments, the glass vial has a shoulder reaction zone upon filling the glass vial ($SHRZ_{0w}$) of no more than 20 nm, and the glass vial has a shoulder reaction zone after storage in the glass vial at 60° C. for 10 weeks ($SH_{10w}$) of no more than 60 nm.

In some embodiments, the glass vial has a shoulder reaction zone upon filling the glass vial ($SHRZ_{0w}$) of no more than 20 nm, and the glass vial has a shoulder reaction zone after storage in the glass vial at 60° C. for 10 weeks ($SH_{10w}$) of no more than 50 nm.

Medical Uses

In some embodiments, the formulation is suitable for injection. In some embodiments, the formulation is suitable for intravenous injection. In some embodiments, the kit is used in diagnosis of an ophthalmic disease or condition. In some embodiments, the kit is used in fluorescein angiography.

Certain Terminology

As used herein, the term "about" is used synonymously with the term "approximately." Illustratively, the use of the term "about" with regard to a specific amount indicates values slightly outside the cited values, e.g., plus or minus 0.1% to 10%. In some embodiments, "about" indicates values that are plus or minus 10%.

The term "acceptable" with respect to a formulation, composition or ingredient, as used herein, means having no persistent detrimental effect on the general health of the subject being treated.

The term "carrier," as used herein, refers to relatively nontoxic chemical compounds or agents that facilitate the incorporation of a compound into cells or tissues.

The terms "co-administration" or the like, as used herein, are meant to encompass administration of the selected therapeutic agents to a single patient, and are intended to include treatment regimens in which the agents are administered by the same or different route of administration or at the same or different time.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one embodiment, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

As used herein, the following terms have the following meanings: NA=not available; ND=not detected; RRT=relative retention time; Q.S=quantity sufficient; and NMT=not more than.

All of the various embodiments or options described herein can be combined in any and all variations. The following Examples serve only to illustrate the invention and are not to be construed in any way to limit the invention.

NON-LIMITING EMBODIMENTS

The disclosure is illustrated herein by the following embodiments, which should not be construed as limiting. Those skilled in the art will understand that this disclosure may be embodied in many different forms and should not be construed as limited to the embodiments set forth herein.

1. A kit, comprising:
    an aqueous formulation comprising from about 50 mg/mL to about 300 mg/mL fluorescein sodium, wherein the formulation has a pH of from about 8 to about 10; and
    a glass vial holding the aqueous formulation,
wherein the aqueous formulation has a dissolved silicon concentration upon filling the glass vial ($Si_{0w}$), and a dissolved silicon concentration after storage in the glass vial at 60° C. for 10 weeks ($Si_{10w}$), wherein $Si_{10w}/Si_{0w}$ is from 1 to 1.6.

2. The kit of Embodiment 1, wherein $Si_{10w}/Si_{0w}$ is from 1 to 1.5.
3. The kit of Embodiment 1, wherein $Si_{10w}/Si_{0w}$ is from 1 to 1.4.
4. The kit of Embodiment 1, wherein $Si_{10w}/Si_{0w}$ is from 1 to 1.3.
5. The kit of Embodiment 1, wherein $Si_{10w}/Si_{0w}$ is from 1 to 1.25.
6. The kit of Embodiment 1, wherein $Si_{10w}/Si_{0w}$ is from 1 to 1.22.
7. The kit of Embodiment 1-6, wherein $Si_{10w}$ is less than 14 mg/L.
8. The kit of Embodiment 1-6, wherein $Si_{10w}$ is less than 13.5 mg/L.
9. The kit of Embodiment 1-6, wherein $Si_{10w}$ is less than 13 mg/L.
10. The kit of Embodiment 1-6, wherein $Si_{10w}$ is less than 12.5 mg/L.
11. The kit of Embodiment 1-6, wherein $Si_{10w}$ is less than 12 mg/L.
12. The kit of Embodiment 1-6, wherein $Si_{10w}$ is less than 11.5 mg/L.
13. A kit, comprising:
    an aqueous formulation comprising from about 50 mg/mL to about 300 mg/mL fluorescein sodium, wherein the formulation has a pH of from about 8 to about 10; and
    a glass vial holding the aqueous formulation,
wherein the aqueous formulation has a dissolved boron concentration upon filling the glass vial ($B_{0w}$), and a dissolved boron concentration after storage in the glass vial at 60° C. for 10 weeks ($B_{10w}$), wherein $B_{10w}/B_{0w}$ is from 1 to 1.9.
14. The kit of Embodiment 13, wherein $B_{10w}/B_{0w}$ is from 1 to 1.8.
15. The kit of Embodiment 13, wherein $B_{10w}/B_{0w}$ is from 1 to 1.7.
16. The kit of Embodiment 13, wherein $B_{10w}/B_{0w}$ is from 1 to 1.6.
17. The kit of Embodiment 13, wherein $B_{10w}/B_{0w}$ is from 1 to 1.5.
18. The kit of Embodiment 13, wherein $B_{10w}/B_{0w}$ is from 1 to 1.4.
19. The kit of Embodiment 13, wherein $B_{10w}/B_{0w}$ is from 1 to 1.3.
20. The kit of Embodiment 13-19, wherein $B_{10w}$ is less than 2.2 mg/L.
21. The kit of Embodiment 13-19, wherein $B_{10w}$ is less than 2.1 mg/L.
22. The kit of Embodiment 13-19, wherein $B_{10w}$ is less than 2.0 mg/L.
23. The kit of Embodiment 13-19, wherein $B_{10w}$ is less than 1.9 mg/L.
24. The kit of Embodiment 13-19, wherein $B_{10w}$ is less than 1.85 mg/L.
25. A kit, comprising:
    an aqueous formulation comprising from about 50 mg/mL to about 300 mg/mL fluorescein sodium, wherein the formulation has a pH of from about 8 to about 10; and
    a glass vial holding the aqueous formulation,
wherein the aqueous formulation has a dissolved silicon concentration upon filling the glass vial ($Si_{0w}$), and a dissolved silicon concentration after storage in the glass vial at 60° C. for 10 weeks ($Si_{10w}$), wherein $Si_{10w}/Si_{0w}$ is from 1 to 1.6, and wherein the aqueous formulation has a dissolved boron concentration upon filling the glass vial ($B_{0w}$), and a dissolved boron concentration after storage in the glass vial at 60° C. for 10 weeks ($B_{10w}$), wherein $B_{10w}/B_{0w}$ is from 1 to 1.9.

26. The kit of Embodiment 25, wherein $Si_{10w}/Si_{0w}$ is from 1 to 1.5.
27. The kit of Embodiment 25, wherein $Si_{10w}/Si_{0w}$ is from 1 to 1.4.
28. The kit of Embodiment 25, wherein $Si_{10w}/Si_{0w}$ is from 1 to 1.3.
29. The kit of Embodiment 25, wherein $Si_{10w}/Si_{0w}$ is from 1 to 1.25.
30. The kit of Embodiment 25, wherein $Si_{10w}/Si_{0w}$ is from 1 to 1.22.
31. The kit of Embodiment 25-30, wherein $Si_{10w}$ is less than 14 mg/L.
32. The kit of Embodiment 25-30, wherein $Si_{10w}$ is less than 13.5 mg/L.
33. The kit of Embodiment 25-30, wherein $Si_{10w}$ is less than 13 mg/L.
34. The kit of Embodiment 25-30, wherein $Si_{10w}$ is less than 12.5 mg/L.
35. The kit of Embodiment 25-30, wherein $Si_{10w}$ is less than 12 mg/L.
36. The kit of Embodiment 25-30, wherein $Si_{10w}$ is less than 11.5 mg/L.
37. The kit of Embodiment 25-36, wherein $B_{10w}/B_{0w}$ is from 1 to 1.8.
38. The kit of Embodiment 25-36, wherein $B_{10w}/B_{0w}$ is from 1 to 1.7.
39. The kit of Embodiment 25-36, wherein $B_{10w}/B_{0w}$ is from 1 to 1.6.
40. The kit of Embodiment 25-36, wherein $B_{10w}/B_{0w}$ is from 1 to 1.5.
41. The kit of Embodiment 25-36, wherein $B_{10w}/B_{0w}$ is from 1 to 1.4.
42. The kit of Embodiment 25-36, wherein $B_{10w}/B_{0w}$ is from 1 to 1.3.
43. The kit of Embodiment 25-42, wherein $B_{10w}$ is less than 2.2 mg/L.
44. The kit of Embodiment 25-42, wherein $B_{10w}$ is less than 2.1 mg/L.
45. The kit of Embodiment 25-42, wherein $B_{10w}$ is less than 2.0 mg/L.
46. The kit of Embodiment 25-42, wherein $B_{10w}$ is less than 1.9 mg/L.
47. The kit of Embodiment 25-42, wherein $B_{10w}$ is less than 1.85 mg/L.
48. A kit, comprising:
   an aqueous formulation comprising from about 50 mg/mL to about 300 mg/mL fluorescein sodium, wherein the formulation has a pH of from about 8 to about 10; and
   a glass vial holding the aqueous formulation,
   wherein the glass vial has a bottom reaction zone upon filling the glass vial ($BTRZ_{0w}$) of no more than 20 nm, and the glass vial has a bottom reaction zone after storage in the glass vial at 60° C. for 10 weeks ($BTRZ_{10w}$) of no more than 250 nm.
49. The kit of Embodiment 48, wherein $BTRZ_{10w}$ is no more than 200 nm.
50. The kit of Embodiment 48, wherein $BTRZ_{10w}$ is no more than 180 nm.
51. The kit of Embodiment 48, wherein $BTRZ_{10w}$ is no more than 160 nm.
52. The kit of Embodiment 48, wherein $BTRZ_{10w}$ is no more than 150 nm.
53. The kit of Embodiment 48, wherein $BTRZ_{10w}$ is no more than 140 nm.
54. The kit of Embodiment 48, wherein $BTRZ_{10w}$ is no more than 130 nm.
55. The kit of Embodiment 48, wherein $BTRZ_{10w}$ is no more than 100 nm.
56. The kit of Embodiment 48, wherein $BTRZ_{10w}$ is no more than 50 nm.
57. The kit of Embodiment 48, wherein $BTRZ_{10w}$ is no more than 40 nm.
58. The kit of Embodiment 48, wherein $BTRZ_{10w}$ is no more than 30 nm.
59. The kit of Embodiment 48, wherein $BTRZ_{10w}$ is no more than 20 nm.
60. The kit of Embodiment 48, wherein $BTRZ_{10w}$ is no more than 10 nm.
61. The kit of Embodiment 48-60, wherein $BTRZ_{0w}$ is no more than 30 nm.
62. The kit of Embodiment 48-60, wherein $BTRZ_{0w}$ is no more than 20 nm.
63. The kit of Embodiment 48-60, wherein $BTRZ_{0w}$ is no more than 10 nm.
64. The kit of Embodiment 48-63, wherein the aqueous formulation has a dissolved silicon concentration upon filling the glass vial ($Si_{0w}$), and a dissolved silicon concentration after storage in the glass vial at 60° C. for 10 weeks ($Si_{10w}$), wherein $Si_{10w}/Si_{0w}$ is from 1 to 1.6.
65. The kit of Embodiment 65, wherein $Si_{10w}/Si_{0w}$ is from 1 to 1.5.
66. The kit of Embodiment 65, wherein $Si_{10w}/Si_{0w}$ is from 1 to 1.4.
67. The kit of Embodiment 65, wherein $Si_{10w}/Si_{0w}$ is from 1 to 1.3.
68. The kit of Embodiment 65, wherein $Si_{10w}/Si_{0w}$ is from 1 to 1.25.
69. The kit of Embodiment 65, wherein $Si_{10w}/Si_{0w}$ is from 1 to 1.22.
70. The kit of Embodiment 64-69, wherein $Si_{10w}$ is less than 14 mg/L.
71. The kit of Embodiment 64-69, wherein $Si_{10w}$ is less than 13.5 mg/L.
72. The kit of Embodiment 64-69, wherein $Si_{10w}$ is less than 13 mg/L.
73. The kit of Embodiment 64-69, wherein $Si_{10w}$ is less than 12.5 mg/L.
74. The kit of Embodiment 64-69, wherein $Si_{10w}$ is less than 12 mg/L.
75. The kit of Embodiment 64-69, wherein $Si_{10w}$ is less than 11.5 mg/L.
76. The kit of Embodiment 48-75, wherein the aqueous formulation has a dissolved boron concentration upon filling the glass vial ($B_{0w}$), and a dissolved boron concentration after storage in the glass vial at 60° C. for 10 weeks ($B_{10w}$), wherein $B_{10w}/B_{0w}$ is from 1 to 1.9.
77. The kit of Embodiment 76, wherein $B_{10w}/B_{0w}$ is from 1 to 1.8.
78. The kit of Embodiment 76, wherein $B_{10w}/B_{0w}$ is from 1 to 1.7.
79. The kit of Embodiment 76, wherein $B_{10w}/B_{0w}$ is from 1 to 1.6.
80. The kit of Embodiment 76, wherein $B_{10w}/B_{0w}$ is from 1 to 1.5.

81. The kit of Embodiment 76, wherein $B_{10w}/B_{0w}$ is from 1 to 1.4.
82. The kit of Embodiment 76, wherein $B_{10w}/B_{0w}$ is from 1 to 1.3.
83. The kit of Embodiment 76-82, wherein $B_{10w}$ is less than 2.2 mg/L.
84. The kit of Embodiment 76-82, wherein $B_{10w}$ is less than 2.1 mg/L.
85. The kit of Embodiment 76-82, wherein $B_{10w}$ is less than 2.0 mg/L.
86. The kit of Embodiment 76-82, wherein $B_{10w}$ is less than 1.9 mg/L.
87. The kit of Embodiment 76-82, wherein $B_{10w}$ is less than 1.85 mg/L.
88. The kit of Embodiment 1-87, wherein the aqueous formulation comprising from about 70 mg/mL to about 130 mg/mL of fluorescein sodium.
89. The kit of Embodiment 1-87, wherein the aqueous formulation comprising from about 90 mg/mL to about 110 mg/mL of fluorescein sodium.
90. The kit of Embodiment 1-87, wherein the aqueous formulation comprising about 100 mg/mL of fluorescein sodium.
91. The kit of Embodiment 1-87, wherein the aqueous formulation comprising from about 200 mg/mL to about 300 mg/mL of fluorescein sodium.
92. The kit of Embodiment 1-87, wherein the aqueous formulation comprising from about 230 mg/mL to about 270 mg/mL of fluorescein sodium.
93. The kit of Embodiment 1-87, wherein the aqueous formulation comprising about 250 mg/mL of fluorescein sodium.
94. The kit of Embodiment 1-93, wherein the aqueous formulation comprises at least one pH adjusting agent.
95. The kit of Embodiment 94, wherein the at least one pH adjusting agent comprises sodium hydroxide, hydrochloric acid, or a combination thereof.
96. The kit of Embodiment 1-95, wherein the aqueous formulation is a solution.
97. The kit of Embodiment 1-96, wherein the glass vial is sealed.
98. The kit of Embodiment 1-97, wherein the glass vial has a fill volume of from 2 mL to 5 mL.
99. The kit of Embodiment 1-97, wherein the glass vial has a fill volume of 5 mL.
100. The kit of Embodiment 1-99, wherein the glass vial is a Schott DC vial.
101. The kit of Embodiment 1-99, wherein the glass vial is made from Fiolax glass and comprises a strengthened shoulder to reduce delamination.
102. The kit of Embodiment 1-101, wherein the glass vial has a shoulder reaction zone upon filling the glass vial ($SHRZ_{0w}$) of no more than 20 nm, and the glass vial has a shoulder reaction zone after storage in the glass vial at 60° C. for 10 weeks ($SH_{10w}$) of no more than 250 nm.
103. The kit of Embodiment 1-101, wherein the glass vial has a shoulder reaction zone upon filling the glass vial ($SHRZ_{0w}$) of no more than 20 nm, and the glass vial has a shoulder reaction zone after storage in the glass vial at 60° C. for 10 weeks ($SH_{10w}$) of no more than 200 nm.
104. The kit of Embodiment 1-101, wherein the glass vial has a shoulder reaction zone upon filling the glass vial ($SHRZ_{0w}$) of no more than 20 nm, and the glass vial has a shoulder reaction zone after storage in the glass vial at 60° C. for 10 weeks ($SH_{10w}$) of no more than 190 nm.
105. The kit of Embodiment 1-101, wherein the glass vial has a shoulder reaction zone upon filling the glass vial ($SHRZ_{0w}$) of no more than 20 nm, and the glass vial has a shoulder reaction zone after storage in the glass vial at 60° C. for 10 weeks ($SH_{10w}$) of no more than 180 nm.
106. The kit of Embodiment 1-101, wherein the glass vial has a shoulder reaction zone upon filling the glass vial ($SHRZ_{0w}$) of no more than 20 nm, and the glass vial has a shoulder reaction zone after storage in the glass vial at 60° C. for 10 weeks ($SH_{10w}$) of no more than 170 nm.
107. The kit of Embodiment 1-101, wherein the glass vial has a shoulder reaction zone upon filling the glass vial ($SHRZ_{0w}$) of no more than 20 nm, and the glass vial has a shoulder reaction zone after storage in the glass vial at 60° C. for 10 weeks ($SH_{10w}$) of no more than 160 nm.
108. The kit of Embodiment 1-101, wherein the glass vial has a shoulder reaction zone upon filling the glass vial ($SHRZ_{0w}$) of no more than 20 nm, and the glass vial has a shoulder reaction zone after storage in the glass vial at 60° C. for 10 weeks ($SH_{10w}$) of no more than 150 nm.
109. The kit of Embodiment 1-101, wherein the glass vial has a shoulder reaction zone upon filling the glass vial ($SHRZ_{0w}$) of no more than 20 nm, and the glass vial has a shoulder reaction zone after storage in the glass vial at 60° C. for 10 weeks ($SH_{10w}$) of no more than 140 nm.
110. The kit of Embodiment 1-101, wherein the glass vial has a shoulder reaction zone upon filling the glass vial ($SHRZ_{0w}$) of no more than 20 nm, and the glass vial has a shoulder reaction zone after storage in the glass vial at 60° C. for 10 weeks ($SH_{10w}$) of no more than 100 nm.
111. The kit of Embodiment 1-101, wherein the glass vial has a shoulder reaction zone upon filling the glass vial ($SHRZ_{0w}$) of no more than 20 nm, and the glass vial 80 nm.
112. The kit of Embodiment 1-101, wherein the glass vial has a shoulder reaction zone upon filling the glass vial ($SHRZ_{0w}$) of no more than 20 nm, and the glass vial has a shoulder reaction zone after storage in the glass vial at 60° C. for 10 weeks ($SH_{10w}$) of no more than 60 nm.
113. The kit of Embodiment 1-101, wherein the glass vial has a shoulder reaction zone upon filling the glass vial ($SHRZ_{0w}$) of no more than 20 nm, and the glass vial has a shoulder reaction zone after storage in the glass vial at 60° C. for 10 weeks ($SH_{10w}$) of no more than 50 nm.
114. The kit of Embodiment 1-113, wherein the aqueous formulation has a pH of from about 8.0 to about 9.8.
115. The kit of Embodiment 1-114, wherein the formulation is suitable for injection.
116. The kit of Embodiment 1-114, wherein the formulation is suitable for intravenous injection
117. The kit of Embodiment 1-116, for use in diagnosis of an ophthalmic disease or condition.
118. The kit of Embodiment 1-116, for use in fluorescein angiography.
119. The kit of Embodiment 1-116, for use in angioscopy of the retina and iris vasculature.
120. The kit of Embodiment 1-116, wherein the glass vial comprises a neck portion having a cylindrical neck wall, a body portion having a cylindrical body wall, and a shoulder portion having a frustoconical shoulder wall that interconnects the neck and body portions, wherein the shoulder wall that extends toward the cylindrical body wall at a transition angle (β) of at least 120°.
121. The kit of Embodiment 120, the frustoconical shoulder wall extends toward the cylindrical body wall at a transition angle (β) of between 120°-170°.
122. The kit of Embodiment 120, the frustoconical shoulder wall extends toward the cylindrical body wall at a transition angle (β) of between 120°-130°.

123. The kit of Embodiment 120, the frustoconical shoulder wall extends toward the cylindrical body wall at a transition angle (β) of between 130°-140°.
124. The kit of Embodiment 120, the frustoconical shoulder wall extends toward the cylindrical body wall at a transition angle (β) of between 140°-150°.
125. The kit of Embodiment 120, the frustoconical shoulder wall extends toward the cylindrical body wall at a transition angle (β) of between 150°-160°.
126. The kit of Embodiment 120, the frustoconical shoulder wall extends toward the cylindrical body wall at a transition angle (β) of between 160°-170°.
127. The kit of Embodiment 120-126, wherein the frustoconical shoulder wall extends toward the cylindrical neck wall at a transition angle (α) of at least 120°.
128. The kit of Embodiment 127, the frustoconical shoulder wall extends toward the cylindrical neck wall at a transition angle (α) of between 120°-170°.
129. The kit of Embodiment 127, the frustoconical shoulder wall extends toward the cylindrical neck wall at a transition angle (α) of between 120°-130°.
130. The kit of Embodiment 127, the frustoconical shoulder wall extends toward the cylindrical neck wall at a transition angle (α) of between 130°-140°.
131. The kit of Embodiment 127, the frustoconical shoulder wall extends toward the cylindrical neck wall at a transition angle (α) of between 140°-150°.
132. The kit of Embodiment 127, the frustoconical shoulder wall extends toward the cylindrical neck wall at a transition angle (α) of between 150°-160°.
133. The kit of Embodiment 127, the frustoconical shoulder wall extends toward the cylindrical neck wall at a transition angle (α) of between 160°-170°.

NON-LIMITING EXAMPLES

The disclosure is illustrated herein by the experiments described by the following examples, which should not be construed as limiting. Those skilled in the art will understand that this disclosure may be embodied in many different forms and should not be construed as limited to the examples set forth herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 1—Fluorescein Injectable Formulation on Market

One commercialized fluorescein injectable product is available through Alcon, Inc. under the name "FLUORESCITE®." Reproduced below is information on the formulation.

FLUORESCITE® (fluorescein injection, USP) 10% contains fluorescein sodium (equivalent to fluorescein 10% w/v). It is a sterile solution for use intravenously as a diagnostic aid. Its chemical name is spiro[isobenzofuran-1(3H),9'-[9-H]xanthene]-3-one, 3'6'-dihydroxy, disodium salt. The active ingredient is represented by the chemical structure:

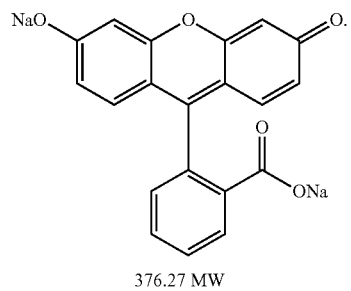

376.27 MW

FLUORESCITE® (fluorescein injection, USP) 10% is supplied as a sterile, unpreserved, unit dose aqueous solution, that has a pH of 8.0-9.8 and an osmolality of 572-858 mOsm/kg.
Active ingredient fluorescein sodium
inactive Ingredients: Sodium hydroxide and/or hydrochloric acid (to adjust pH), and water for injection.

Example 2—Fluorescein Injectable Product on Market

Additionally, information on how the FLUORESCITE® formulation is supplied and stored is provided below.
FLUORESCITE® (fluorescein injection, USP) 10% is supplied in a single-dose 5 mL glass vial with a gray FluroTec® coated chlorobutyl stopper and purple flip-off aluminum seal. The vial stopper is not made with natural rubber latex. The vial contains a sterile, red-orange solution of fluorescein.
FLUORESCITE® (fluorescein injection, USP) 10% Storage and Handlings: Store at 2° C. to 25° C. (36° F. to 77° F.).

Example 3—Glass Delamination/Contamination Study Design/Protocol

The present disclosure provides compatibility testing for drug products in glass vials including a delamination screening package aligned with USP <790>, USP <1660>, and EP 3.2.1. recommendations. The design of such studies provides reliable data for risk assessment for drug container compatibility. The factor for the suitability of such investigations is the categorization of different observations with respect to their criticality and that features need to be found which are early indicators for the later occurrence of delamination.

The containers to be tested and filled with drug product or placebo solution, can be drawn from real-time stability studies or stored under accelerated ageing conditions. The extent of glass corrosion and chemical attack is assessed by analyses of the inner glass surface morphology, the concentrations of extracted elements in solution, and by identification of particles and flakes. Exemplary analytical techniques are described and illustrated herein.

Figure 6:
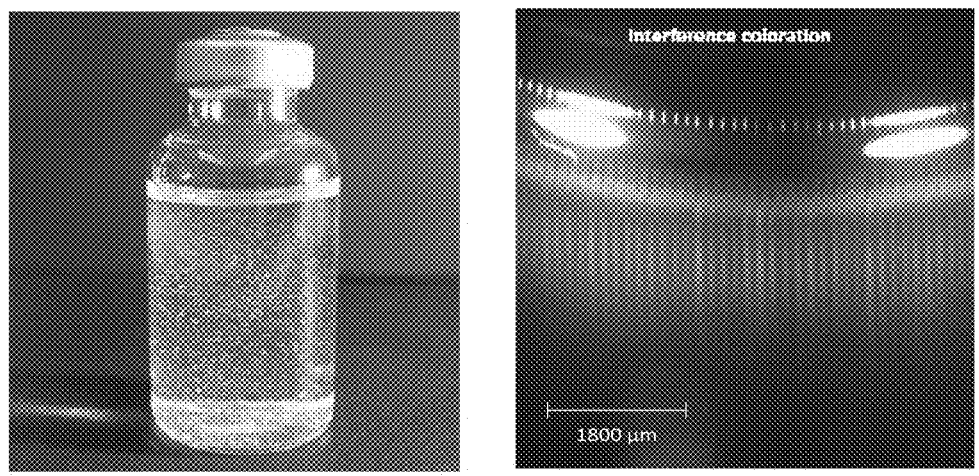
FIG. 6 illustrates visual and optical inspection of a sample vial unrelated to the present disclosure.

Visual and Optical Inspection
This analytical technique is used to detect particles via visual inspection by eye and camera (filled vials) and to visualize coloration and scattering (for empty and for emptied vials). This allows for the identification of containers with high particle load and with changed surface and surface near regions to determine the worst samples of a set by stereo-microscopy. FIG. 6 illustrates visual and optical inspection of a sample unrelated to the present disclosure.

SEM Cross-Section Analysis

Figures 7, 8:
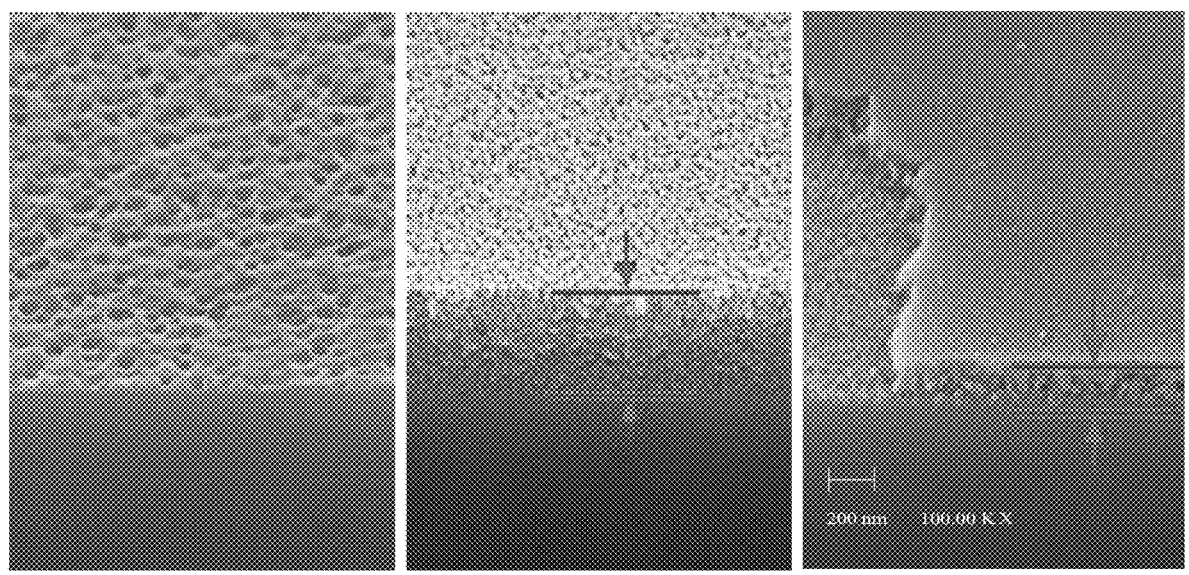
FIG. 7 illustrates SEM analysis of a sample vial unrelated to the present disclosure.
FIG. 8 illustrates ICP analysis of a sample vial unrelated to the present disclosure.

This analytical technique is used to determine the extent of chemical attack of inner glass surface and of surface near regions. This allows for classification between different levels of glass corrosion. Typical features are roughening, formation of reaction zones and/or delaminated areas at the interior surface in contact with the drug product. FIG. 7 illustrates SEM analysis of a sample unrelated to the present disclosure.

ICP Analysis

This analytical technique is used to quantify the amounts of leached glass elements. Allows for the confirmation of the chemical mechanism of drug container interaction. FIG. 8 illustrates ICP analysis of a sample unrelated to the present disclosure.

SEM/EDS and Raman Microscopy

This analytical technique is used to analyze the composition of particles after filtration. This allows identification of morphology (SEM), elemental components (SEM/EDS), and molecular structure (Raman) of isolated particles to distinguish between glass flakes and other particles.

Study Protocol

An exemplary delamination study protocol is provided below.

Step 1: Visual inspection by eye and magnifying video camera with respect to the presence of particles or flakes (10 filled vials per time point according to Tables 1+2).

Step 2: Optical inspection of emptied containers per time point: Stereo-microscopy with extended depth of focus to qualitatively determine if there are any indications for reaction zones or scattering present on the interior surface (10 vials per time point according to Tables 1+2). Selection of two "worst" samples on the basis of stereo-microscopic inspection for subsequent SEM cross-section analyses.

Step 3: SEM (scanning electron microscopy) cross-section analyses on the interior surface of two "worst" vials for selected test conditions and selected time points as described in Tables 1+2; analyses of three areas: wall near bottom, middle of the vial body, and wall near shoulder. These investigations reveal the presence of a potential reaction zone.

Step 4: ICP (inductively coupled plasma) analyses of 10 mL drug solution pooled from the vials of each batch for selected test conditions and selected time points according to Tables 1+2 to quantitatively determine the amount of "glass" elements leached into solution for selected "glass" elements (e.g. Si, B, Ca, Al) to ascertain if the amounts and ratios found are normal or if there is a pronounced chemical attack.

Step 5: Filtration of the solution of one selected vial through a silver membrane (pore size approx. 0.2 µm) using a vacuum filtration unit. Subsequent SEM/EDS and Raman analyses of found particulate matter to determine the elemental composition and morphology of the particles by SEM/EDS and the molecular structure by match of Raman signals to library.

Optional Step 6 (if the mechanism of glass corrosion is unclear or reaction zones are observed): SIMS (secondary ion mass spectrometry) depth profiling of the interior surface to get information about the composition of the surface near region.

In some cases, the protocol described above are applied at different time points under accelerated storage conditions. These conditions are defined on the basis of the drug product application and customer requirements.

Example 4—Delamination/Contamination Study of RLD Vials and Fortis Vials

A glass delamination testing in accordance with USP <1660> for "Fluorescein Injection 10%" in two vial presentations: 5 mL clear molded conventional vial (RLD) and an improved vials (Fortis 4R clear vial) converted from SCHOTT Fiolax CHR tubing. The shelf-life of the drug product is 24 months at 25° C. and its pH range is 8.0-9.8. The formulation contains fluorescein sodium, water, hydrochloric acid and/or sodium hydroxide for pH adjustment. The filled vial undergoes terminal sterilization. The delamination screening study was performed at 60° C. to determine if there is any evidence for glass delamination, predelamination, or glass attack by the formulation. In addition, characterization of the conventional vial (RLD) with respect to composition, the glass type, and identifying in a best effort approach the glass manufacturer based on published glass compositions. The samples were analyzed with respect to indications for glass delamination in alignment with the recommendations of the USP <1660>.

1. Samples

TABLE 1

List of samples

| Sample set No. | Sample identification | Description |
| --- | --- | --- |
| 01 | AK-FLUOR ® 10% Fluorescein InjectionUSP, 100 mg/mL, NDC 17478-253-10 LOT: 021576A, EXP: Feb. 2018 Manufactured by: Akorn, Inc. | RLD vials |
| 02 | Container: 5 mL Unprinted Clear Glass Fortis Zenith (Soffieria Bertolini) Mfg Date: 7 Aug. 2019 | Empty control vials |
| 03 | Fluorescein Injection, USP 10% w/v, 100 mg/mL, 5 mLB.No: FLUO15PG1/013 Mfg Date: 7 Aug. 2019 | Fortis, t0: initial vials |
| 04 | Fluorescein Injection, USP 10% w/v, 100 mg/mL, 5 mLB.No: FLUO15PG1/013 Mfg Date: 7 Aug. 2019 | Fortis, t1: 5 weeks, 60° C. |
| 05 | Fluorescein Injection, USP 10% w/v, 100 mg/mL, 5 mLB.No: FLUO15PG1/013 Mfg Date: 7 Aug. 2019 | Fortis, t2: 10 weeks, 60° C. |
| 06 | Fluorescein Injection, USP Bulk solution, Filtered in non-glass bottle, B.No: FLUO15PG1/013Mfg Date: 7 AUG. 2019 | Matrix solution |

1.1 Sample Preparation

Removing labels and re-labeling of the samples with a water- and chemical-proofpermanent marker.

Emptying of filled samples after visual inspection.

Rinsing 3 times with hot tap water and 3 times with demineralized water.

Rinsing 5 times isopropanol and 3 times with acetone.

Drying of containers in a laminar air flow cabinet.

Additional for Part 2:

Two vials of sample set 01 were ground and fused to a tablet for semi-quantitative XRF-screening analysis (w/o boron) according to standard operating procedure "SCHOTT_CA_0015". For wet chemical analysis of boron, a chemical glass digestion was performed previously to the analysis according to standard operating procedure "AAW_CA_0521".

2. Study Protocol:

Part 1: Glass Delamination Study (Sample Sets 01-06)

Visual inspection by eye of 10 filled vials of sample sets 01 and 03-05 with respect to the presence/absence of particles in general according to USP <790>/EP 2.9.20. [4]; and visual inspection by eye and magnifying video camera of 10 filled vials of sample sets 01 and 03-05 with respect to the presence/absence of "flake-like" particles (In-house method) [5].

Optical inspection: SM [6] of 10 vials of sample set 01 (molded) with extended depth of focus to determine qualitatively if there are any indications for conspicuous areas present on the sample interior surface. If present, these areas were classified with respect to coloration and light scattering. According to the experiences so far, especially the coloration indicates a delamination risk [7].

Optical inspection by SM [6] of 10 vials of sample sets 03-05 (tubular) and 5 vials of sample set 02 (tubular, controls) with extended depth of focus to determine qualitatively if there are any indications for reaction zones present on the vial interior surface. The optical inspection by means of stereo-microscopy is focused on the wall near bottom and wall near shoulder areas. Within the wall near bottom area, a distinction is made between two neighboring sections A and B, while in the wall near shoulder area, the section C was investigated. The areas were classified with respect to coloration and light scattering. According to the experiences so far, especially the coloration indicates a delamination risk [7].

SEM [8] cross-section analyses at the vial interior surface in the conspicuous areas of the 2 vials of sample set 01 (molded) as identified by stereo-microscopy. If no such areas were present, the analyses were carried out in the wall near bottom, the wall near shoulder, and the reference area (in the mid-body). This investigation reveals the presence or absence of a potential reaction zone [9].

SEM [8] cross-section analyses at the vial interior surface in the vulnerable areas of the 2 "worst" vials of sample sets 02-04 (tubular) as identified by stereo-microscopy. The analyses were carried out in the wall near bottom, wall near shoulder, and a reference area (in the mid-body). This investigation reveals the presence or absence of a potential reaction zone [9].

ICP-MS/-OES [10] analyses of the drug solution pooled from 10 vials of sample sets 01, 03, and 04 to determine quantitatively the concentration of "glass" elements in solution for 4 elements (Al, B, Ca, and Si) to ascertain if the amount found is normal or if there is a pronounced chemical attack. This investigation helps to determine the corrosion mechanism [11].

Part 2: Characterization of One Vial Type (Sample Set 01)

Glass appearance characterization (clear/amber glass, molded/tubular glass).

Determination of chemical composition by XRF [12,13] and wet chemical analysis ($B_2O_3$) [14]. Identification of glass type IA/IB or soda-lime glass and glass manufacturer; if not SCHOTT glass based on published data in a best effort approach SM: Stereo-Microscopy (visual appearance)

SEM: Scanning Electron Microscopy (surface morphology)

ICP-MS/-OES: Inductively Coupled Plasma (-MS Mass Spectrometry, -OES Optical Emission Spectroscopy) (trace analyses within solution)

XRF: X-Ray Fluorescence (determination of composition)

TABLE 2

Test methods for each sample set (with number of vials)

| | | Sample set No./Storage condition | | | | |
|---|---|---|---|---|---|---|
| Method | Guideline | 01 RLD vials | 02 Fortis, empty controls | 03 Fortis, t0: initial | 04 Fortis, t1: 5 weeks, 60° C. | 05 Fortis, t2: 10 weeks, 60° C. |
| Visual Inspection | USP <790>/ EP 2.9.20., USP <1660>, In-house method | 10 | — | 10 | 10 | 10 |
| Stereo-microscopy | USP <1660> | 10 | 5 | 10 | 10 | 10 |
| SEM cross-section analyses | | 2 | 2 | 2 | 2 | No[2] |
| ICP-analyses | | Yes | — | Yes | Yes | No[2] |
| Filtration and SEM/EDS particle analyses | | No[1] | — | No[1] | No[1] | No[2] |
| Glass characterization | | — | Yes | — | — | — |

[1]During visual inspection, no "flake-like" particles were observed by eye. Thus, no filtration and subsequent SEM/EDS particle characterization were conducted.
[2]Customer stopped the study before these methods were conducted.

3. Results 3.1 Sample Set 01 (RLD Vials)

Part 1: Glass Delamination Study

Visual Inspection (Table 5):

The results of the inspection of filled vials by eye and with a magnifying camera are summarized in Table 5. Particles in general were inspected according to USP <790>/EP 2.9.20. at 10,000 lux; "flake-like" particles were characterized by an In-house method. The inspection was done for 10 filled vials of sample set 01.

No "flake-like" particles" were observed by eye and the camera system (In-house method).

In accordance with USP <790>/EP 2.9.20., no particles were seen.

Optical inspection of the "critical" areas using stereo-microscopy (Table 6): The inspection was done for 10 vials of sample set 01. The representative photographs of the two "worst" vials are characterized below.

In the wall near shoulder area, up to medium scattering was observed.

Up to weak scattering was found in the wall near bottom area.

No coloration was present.

Figure 11:
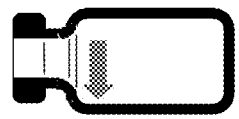
FIG. 11 illustrates SEM analysis of a sample vial according to one embodiment of the present disclosure.
Figure 11:
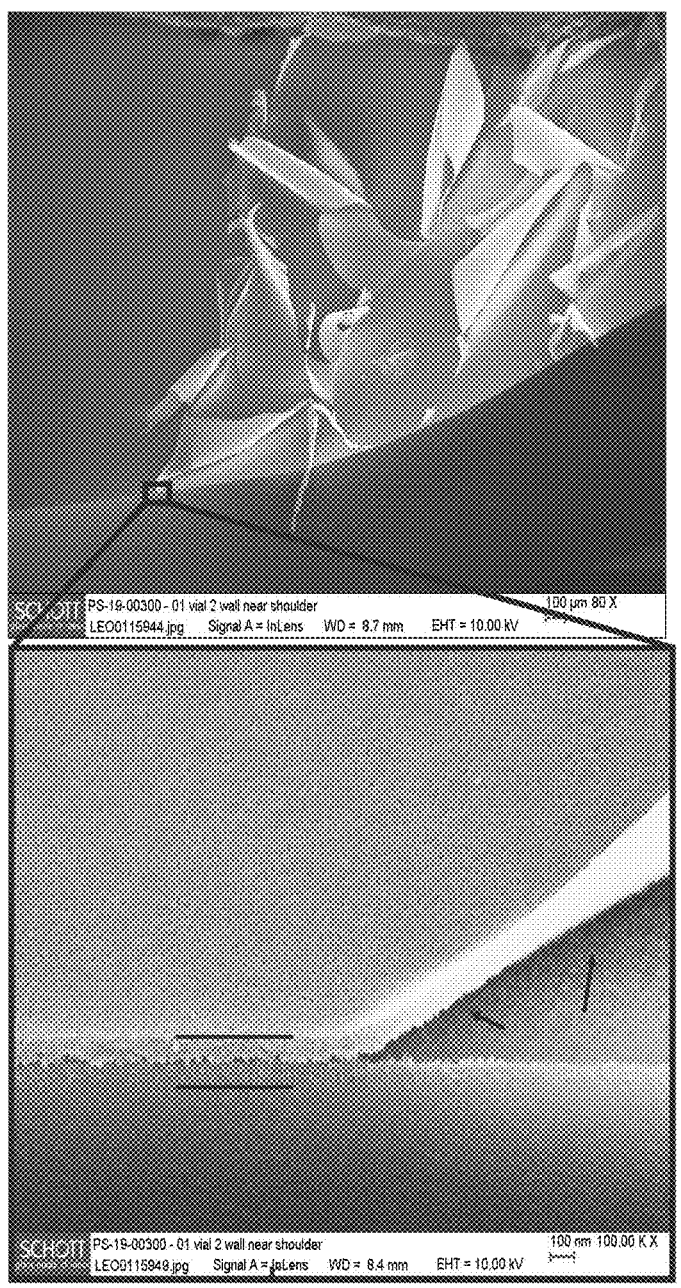
Figure 12:
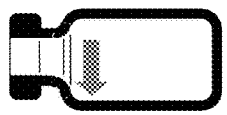
FIG. 12 illustrates SEM analysis of a sample vial according to one embodiment of the present disclosure.
Figure 12:
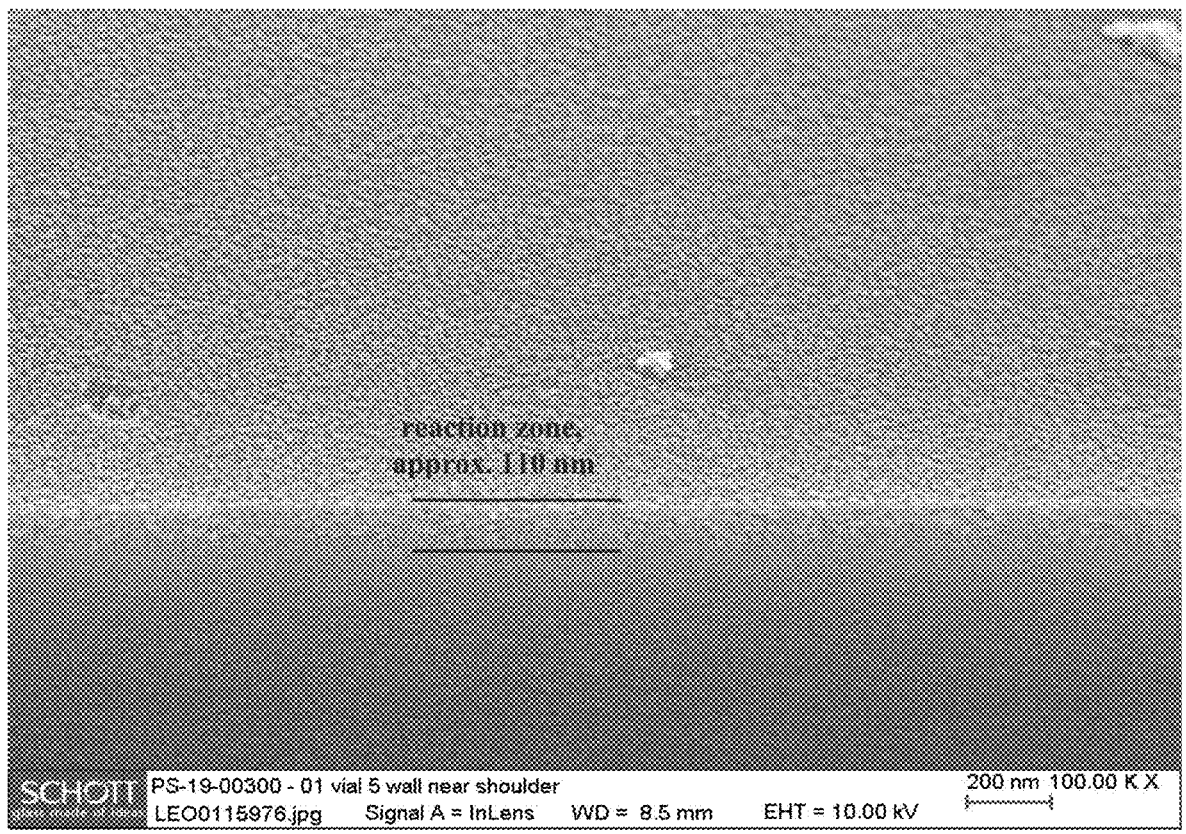

Investigation of the morphology of the interior surface using SEM (FIGS. 11-12 and Table 9): Three areas out of the selected vials were characterized by SEM cross-section analysis (wallnear bottom, wall near shoulder, and reference area). More or less 5 characteristic features werefound: Delaminated areas, reaction zones, micro-roughness, deposits (particulate), and shallowpits. The appearance of the characteristic features is summarized in Table 9.

Delaminated areas and reaction zones with thicknesses up to about 150 nm wereobserved in the wall near shoulder area.

Micro-roughness and deposits (particulate) were found in the wall near shoulder, wallnear bottom, and reference area.

Shallow pits were present in the wall near shoulder and wall near bottom area.

Concentration of Dissolved "Glass" Elements (Table 10):

The entire data set of the ICP measurements is listed in Table 10.

The concentration of Si was about 11 mg/L, the concentration of B about 1.5 mg/L and the concentration of Ca about 0.68 mg/L.

The concentration of Al was below the limit of quantification of 0.05 mg/L.

Part 2: Characterization of One Vial Type

Visual Appearance and Glass Composition by XRF and Wet Chemistry ($B_2O_3$)

From the visual appearance of the vials, sample set 01 can be ascribed to clear molded glass. The concentrations of the glass components measured by XRF and wet chemical analysis for $B_2O_3$ are summarized in Table 11.

TABLE 3

Chemical composition of sample set 01 (RLD vials) in % [w/w]

| Oxide | Method | Sample 01 Concentration |
|---|---|---|
| $Al_2O_3$ | XRF | 5.43 ± 0.11 |
| BaO | XRF | 2.23 ± 0.07 |
| $B_2O_3$ | wet chemistry | 11.77 ± 0.20 |
| CaO | XRF | 1.41 ± 0.03 |
| $Fe_2O_3$ | XRF | 0.046 ± 0.009 |
| $K_2O$ | XRF | 1.12 ± 0.06 |
| MgO | XRF | <0.05 |
| MnO | XRF | 0.041 ± 0.008 |
| $Na_2O$ | XRF | 8.0 ± 0.3 |
| $SiO_2$ | XRF | 69.5 ± 0.5 |
| SrO | XRF | 0.041 ± 0.008 |
| $TiO_2$ | XRF | <0.02 |
| ZnO | XRF | 0.022 ± 0.007 |
| $ZrO_2$ | XRF | 0.064 ± 0.013 |

Note:
The vial was ground and fused to a tablet for semi-quantitative XRF analysis. Easily volatile elements (F, Cl, S, As) can evaporate during melting. Li, C, N, and O cannot bedetermined by XRF analysis. It was assumed that all elements were present as oxides.

3.2 Sample Set 02 and 03 (Empty Controls and t0)

Part 1: Glass Delamination Study

Visual Inspection (Table 5):

The results of the inspection of filled vials by eye and with a magnifying camera are summarized in Table 5. Particles in general were inspected according to USP <790>/EP 2.9.20. at 10,000 lux; "flake-like" particles were characterized by an In-house method. The inspection was done for 10 filled vials of sample set 03.

Up to a few "flake-like" particles were found applying the camera system (In-housemethod).

No "flake-like" particles were observed by eye (In-house method).

In accordance with USP <790>/EP 2.9.20., no particles were seen.

Optical inspection of the "critical" areas using stereo-microscopy (Table 7+8): The inspection was done for 10 vials per sample set. The representative photographs of the two "worst" vials are characterized below.

One vial out of 5 from sample set 02 featured weak coloration in the wall near bottomarea A.

Up to strong scattering was found in the wall near bottom area A for sample set 03, while up to a medium scattering was observed in this area for sample set 02.

Up to medium scattering was present in the wall near bottom area B for sample set 03.

In the wall near shoulder area, up to weak scattering was observed for sample sets 02 and 03.

Figure 13:
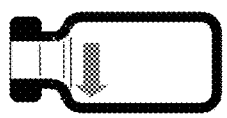
FIG. 13 illustrates SEM analysis of a sample vial according to one embodiment of the present disclosure.
Figure 13:
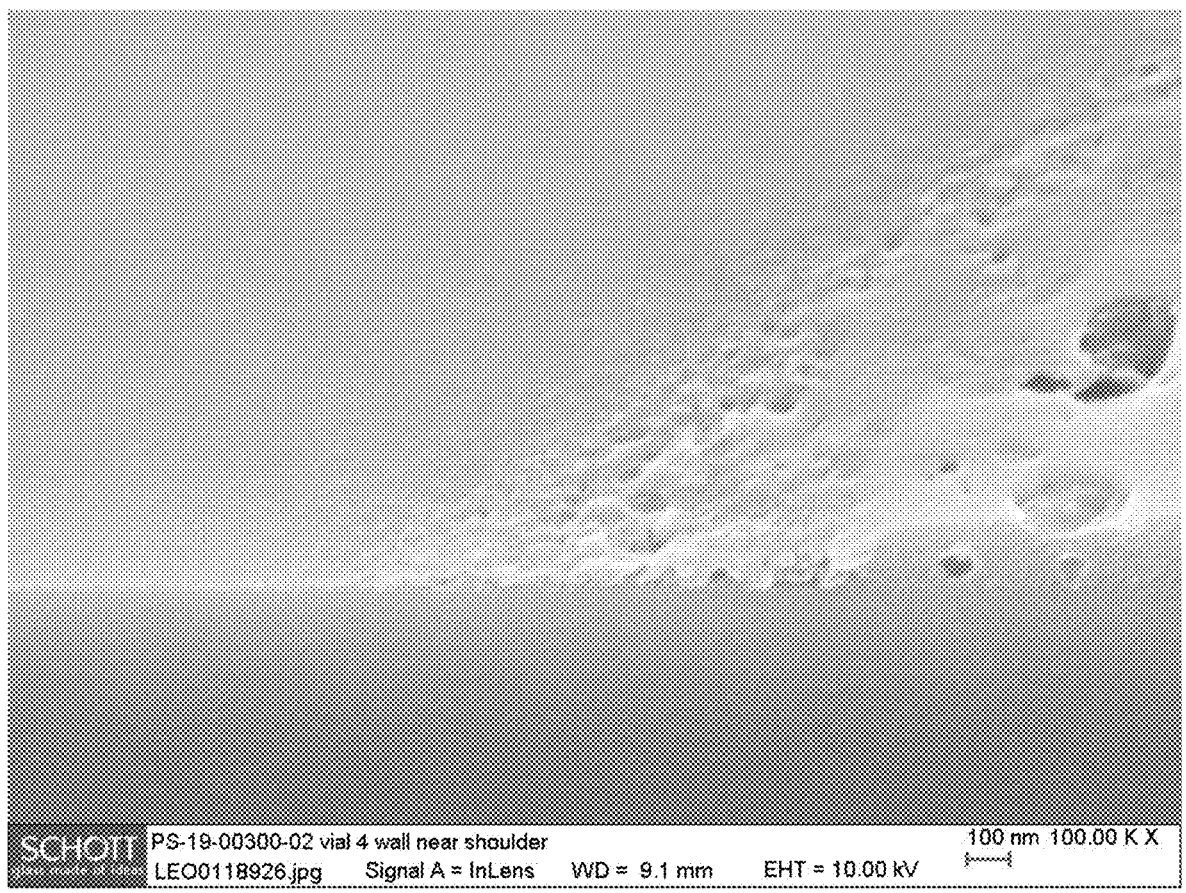
Figure 14:
FIG. 14 illustrates SEM analysis of a sample vial according to one embodiment of the present disclosure.
Figure 14:
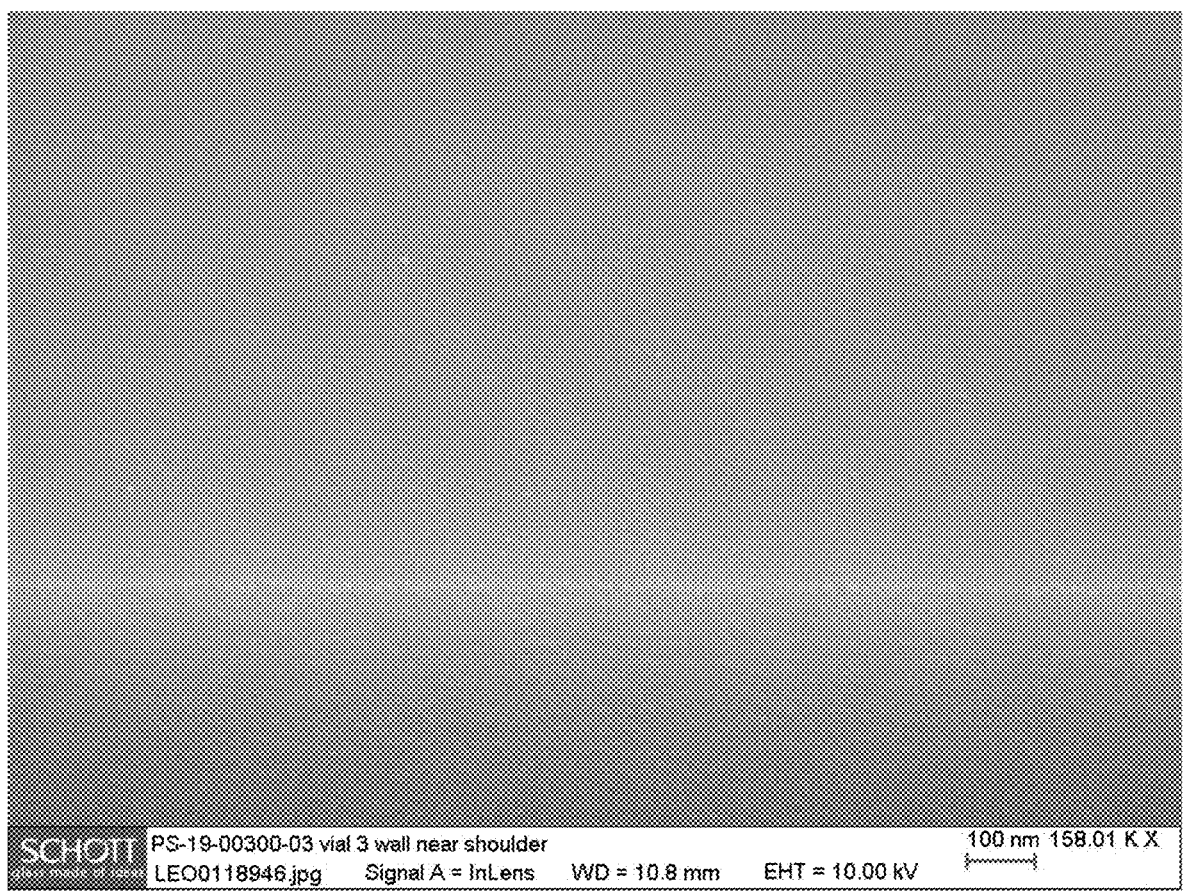
Figure 15:
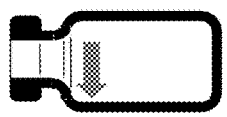
FIG. 15 illustrates SEM analysis of a sample vial according to one embodiment of the present disclosure.
Figure 15:
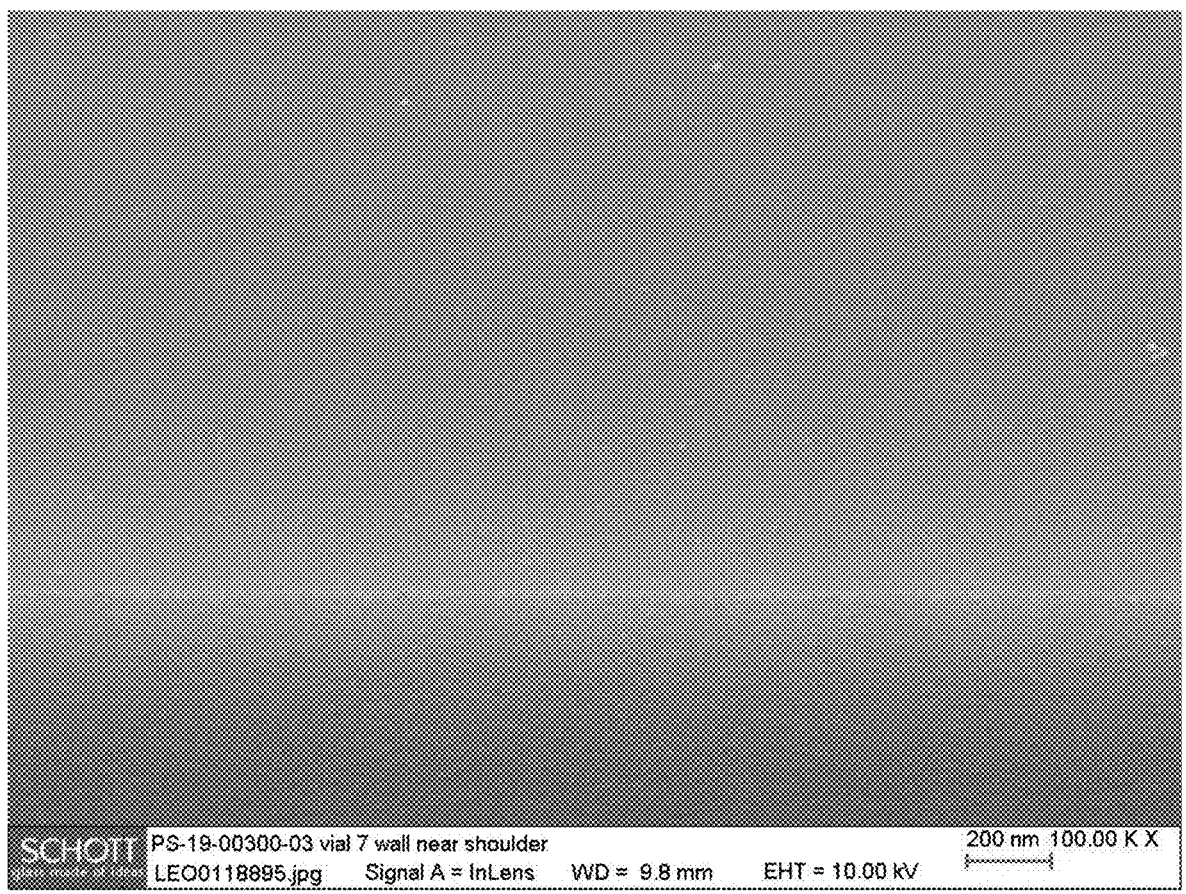

Investigation of the morphology of the interior surface using SEM (FIGS. 13-15 and Table 9): Three areas out of the selected vials were characterized by SEM cross-section analysis (wallnear bottom, wall near shoulder, and reference area). More or less 5 characteristic features werefound: Micro-roughness, deposits (particulate), deposits (planar), shallow bumps, and shallowpits. The appearance of the characteristic features is summarized in Table 9.

Sample set 03 featured micro-roughness in the wall near bottom and reference area, while this feature was observed for sample set 02 in the wall near shoulder area.

Deposits (particulate) and deposits (planar) were found in the wall near shoulder area for sample set 02, while deposits (particulate) were present in the wall near bottom and reference area for sample set 03.

Shallow pits were observed in the wall near shoulder and reference area for sample set 02, while this feature was observed in the wall near bottom area for sample set 03.

Shallow bumps were observed in the reference area for sample set 02.

Concentration of dissolved "glass" elements (Table 10):

The entire data set of the ICP measurements is listed in Table 10.

Matrix solution (sample set 06)

The Ca-concentration was about 2.1 mg/L in the matrix solution.

The concentrations of Al, B, and Si were below the respective limit of quantification.

Initial time point t0 (sample set 03)

Compared to the matrix solution, the concentrations of Si, B, and Al increased significantly above the respective limit of quantification for sample set 03.

The concentration of Ca found for sample set 03 was in agreement with the value obtained for the matrix solution.

3.3 Sample Set 04 (t1: 5 Weeks, 60° C.)

Part 1: Glass Delamination Study

Visual Inspection (Table 5):

The results of the inspection of filled vials by eye and with a magnifying camera are summarized in Table 5. Particles in general were inspected according to USP <790>/EP 2.9.20. at 10,000 lux; "flake-like" particles were characterized by an In-house method. The inspection was done for 10 filled vials of sample set 04.

For one vial out of 10, a few "flake-like" particles were found applying the camerasystem (In-house method).

No "flake-like" particles were observed by eye (In-house method).

In accordance with USP <790>/EP 2.9.20., no particles were seen.

Optical inspection of the "critical" areas using stereomicroscopy (Table 7+8):The inspection was done for 10 vials per sample set. The representative photographs of the two "worst" vials are characterized below.

Up to weak coloration and up to strong scattering were observed in the wall near bottomareas A and B.

In the wall near shoulder area C, no coloration and no scattering were found.

Figure 16:
FIG. 16 illustrates SEM analysis of a sample vial according to one embodiment of the present disclosure.
Figure 16:
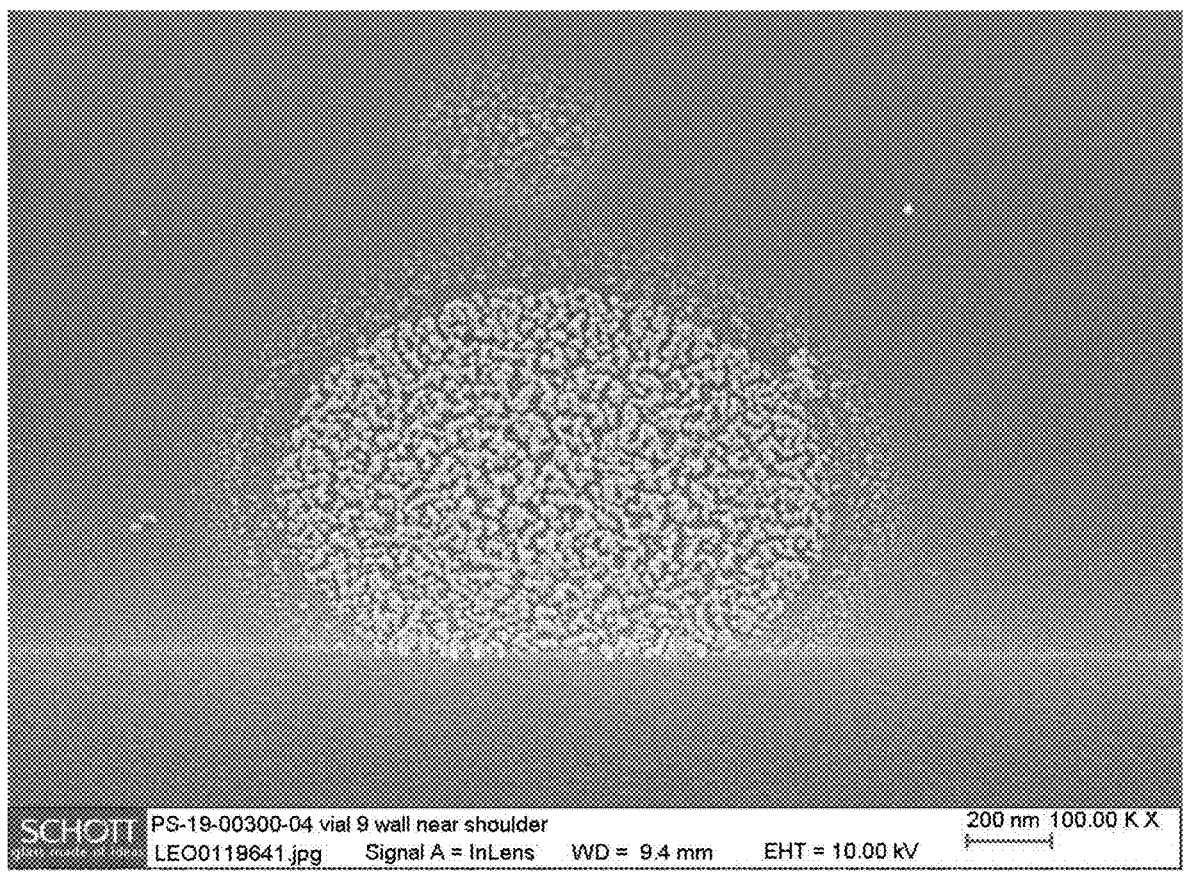
Figure 17:
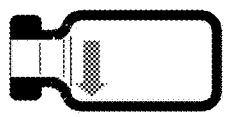
FIG. 17 illustrates SEM analysis of a sample vial according to one embodiment of the present disclosure.
Figure 17:
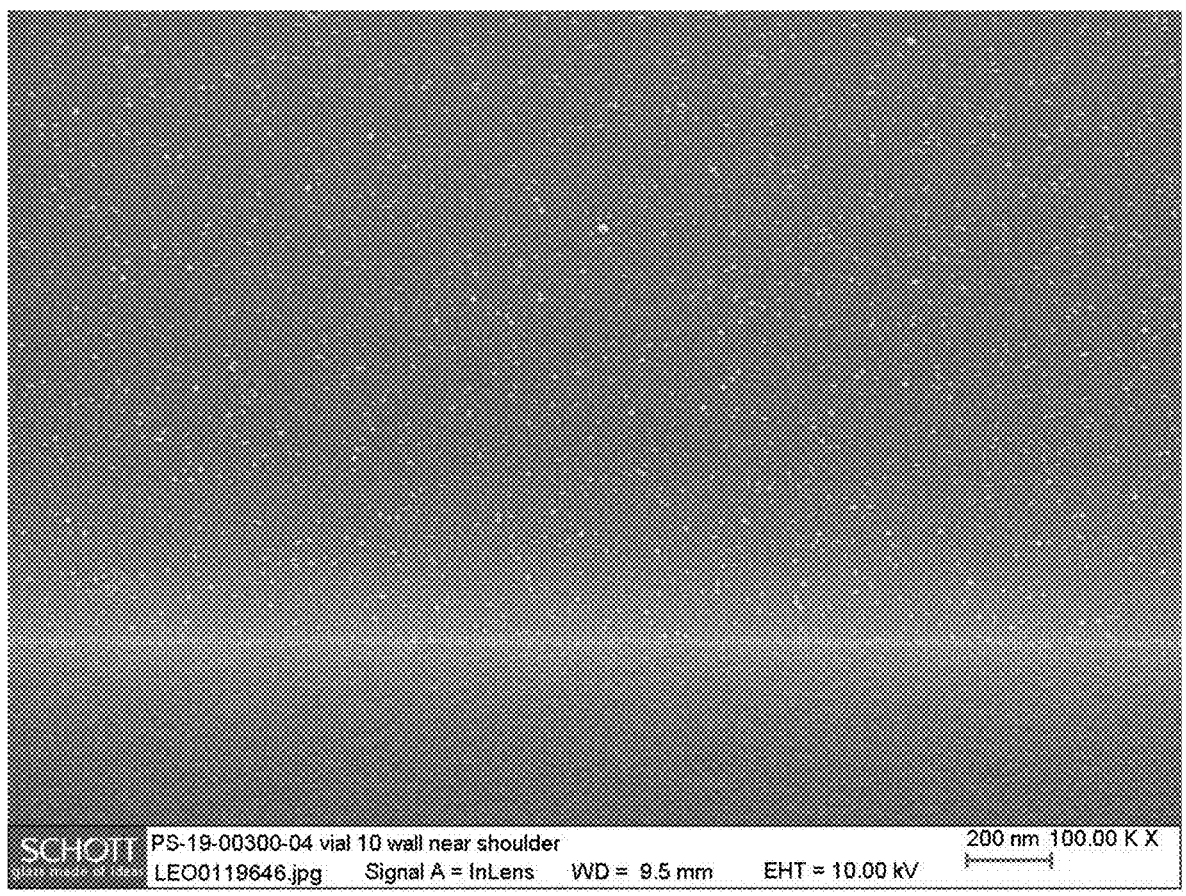

Investigation of the morphology of the interior surface using SEM (FIGS. 16-17 and Table 9): Three areas out of the selected vials were characterized by SEM cross-section analysis (wallnear bottom, wall near shoulder, and reference area). More or less 5 characteristic features werefound: Delaminated areas, reaction zones, micro-roughness, deposits (particulate), and shallowpits. The appearance of the characteristic features is summarized in Table 9.

Delaminated areas, reaction zones with thicknesses up to approx. 470 nm, and micro-roughness were present in the wall near bottom area.

Deposits (particulate) were found in the wall near bottom, wall near shoulder, and reference area.

Shallow pits were observed in the wall near bottom and wall near shoulder area.

Concentration of Dissolved "Glass" Elements (Table 10):

The entire data set of the ICP measurements is listed in Table 10.

Compared to the initial time point (sample set 03), the concentrations of Si (about 13 mg/L) and B (about 2.0 mg/L) increased slightly.

The concentrations of Al (about 0.070 mg/L) and Ca (about 2.2 mg/L) remained constant with respect to the previous time point and considering the measuring uncertainties.

3.4 Sample Set 05 (t2: 10 Weeks, 60° C.)

Part 1: Glass Delamination Study

Visual Inspection (Table 5):

The results of the inspection of filled vials by eye and with a magnifying camera are summarized in Table 5. Particles in general were inspected according to USP <790>/EP 2.9.20. at 10,000 lux; "flake-like" particles were characterized by an In-house method. The inspection was done for 10 filled vials of sample set 05.

For 3 vials out of 10, a few "flake-like" particles were found applying the camera system (In-house method).

No "flake-like" particles were observed by eye (In-house method).

No particles were seen in accordance with USP <790>/EP 2.9.20.

Optical inspection of the "critical" areas using stereomicroscopy (Table 7+8):The inspection was done for 10 vials per sample set. The representative photographs of the two "worst" vials are characterized below.

Up to strong coloration was observed in the wall near bottom area B, while all vials featured weak coloration in the wall near bottom area A.

Up to strong scattering was found in the wall near bottom area A, medium scattering in the wall near bottom area B, and up to weak scattering in the wall near shoulder area C.

4. Interpretation 4.1 Sample Set 01 (RLD Vials)

Delamination was confirmed by delaminated areas that were observed by SEM cross-section analyses for sample set 01. In addition, this sample set featured reaction zones, which are classified as early indicators for delamination. Furthermore, glass attack was observed as micro-roughness and a Si-concentration in solution of about 11 mg/L. This indicates that an alteration to the inner glass surface by the formulation has taken place. Deposits (particulate) were found on the inner surface of the glass containers for sample set 01. This is most probably due to an interaction between the formulation and the interior glass surface, too.

Sample set 01 was made of clear molded glass. Based on the current analyses and considering the measuring uncertainties, it can be confirmed, that the glass composition of sample set 01 was very similar to Type I, class B aluminoborosilicate clear glass within the so-called 5.1 COE class with a coefficient of thermal expansion in the range of 4.8-5.6 [10-6K-1] (see specification in ASTM E 438). Best fit to published glass compositions was found for "Kimble KG-35" and "Bormioli Rocco Type I" clear glass (see Table 11). Due to the numerous suppliers of clear molded glass vials and non-published compositions, other glass manufacturers are feasible, too.

4.2 Sample Sets 02 and 03 (Empty Controls and t0)

No delamination (delaminated areas and/or sharp edges) and no early indicators for delamination (i.e. reaction zones) were confirmed for sample sets 02 and 03. Glass attack was observed as micro-roughness for both sample sets. In addition, sample set 03 featured strong scattering and a Si-concentration of approx. 9.4 mg/L. These three features indicate that an alteration to the inner glass surface by the formulation has taken place. Deposits were found on the inner surface of the glass containers for both sample sets. Due to their appearance, these might be related to a pre-treatment process or the converting process in the case of sample set 02, while these might be caused by an interaction between the drug formulation and the interior glass surface in the case of sample set 03. Shallow pits and shallow bumps are typical converting features of tubular containers and are not considered as critical with respect to delamination.

4.3 Sample Set 04 (t1: 5 Weeks, 60° C.)

SEM cross-section analyses confirmed delamination by the observation of delaminated areasin the wall near bottom area. In addition, early indicators were found as coloration in combination with reaction zones. Glass attack was observed as micro-roughness, strong scattering, and a Si-concentration in solution of about 13 mg/L. These features indicate that an alteration to the inner glass surface by the formulation has taken place. Deposits (particulate) were found on the inner surface of the glass containers. This is most probably dueto an interaction between the formulation and the interior glass surface. Shallow pits are typical features of tubular vials, which were initiated during the converting process and are not considered as critical regarding delamination.

4.4 Sample Set 05 (t2:10 Weeks, 60° C.)

Based on visual inspection and optical inspection by SM, glass attack was confirmed as strong scattering.

TABLE 4

Short summary with respect to delamination

| | Sample set No. | | | | |
|---|---|---|---|---|---|
| Shortage | 01 | 02 | 03 | 04 | 05 |
| | RLD vials | Fortis, empty controls | Fortis, t0: initial | Fortis, t1: 5 weeks, 60° C. | Fortis, t2: 10 weeks, 60° C. |
| Delamination confirmed[a] | Yes | No | No | Yes | — |
| Early indicators for delamination[b] | Yes | No | No | Yes | — |
| Glass attack[c] | Yes | Yes | Yes | Yes | — |
| Others[d] | Yes | Yes | Yes | Yes | Yes |

[a]Delamination confirmed:
Sharp edges or delaminated areas (SEM)
Glass flakes (visual inspection + particle analyses)
Flakes composed of glass elements in combination with formulation components (visual inspection + particle analyses)
[b]Early indicators:
Reaction zone at the interior surface (SEM)
Coloration observed by optical inspection (SM) in combination with reaction zone at the interior surface (SEM)
Si/B concentration ratio below or equal to 5 and Si concentration above 7.1 mg/L (for vial format above 2 mL up to 5 mL)
[c]Glass attack
Micro-roughness of the interior surface (SEM)
Strong scattering observed by optical inspection (SM)
Si concentration above 7.1 mg/L (for vial format above 2 mL up to 5 mL)
[d]Others
Shallow pits, shallow bumps, small holes, deposits (SEM)
Weak-to-medium scattering observed by optical inspection (SM)
Local reaction zone/local delaminated area (lateral dimension below 20 μm) (SEM)
Coloration observed by optical inspection (sm) without reaction zones (SEM)

5. Enclosure

TABLE 5

Summary of the visual inspection of filled vials with respect to "flake-like" particles and particles in general

| | In-house method[1] | | USP <790>/ |
|---|---|---|---|
| Sample set No. | Flakes camera | Flakes eye | EP 2.9.20.[2] Particles |
| 01: RLD vials | 0 (10/10) | 0 (10/10) | No (10/10) |
| 03: Fortis, t0: initial | I (5/10) 0 (5/10) | 0 (10/10) | No (10/10) |
| 04: Fortis, t1: 5 weeks, 60° C. | I (1/10) 0 (9/10) | 0 (10/10) | No (10/10) |
| 05: Fortis, t2: 10 weeks, 60° C. | I (3/10) 0 (7/10) | 0 (10/10) | No (10/10) |

[1]Quantity of flakes: 0 = none, I = a few, II = a lot (The camera system is able to detect much smaller flakes compared to the inspection by eye).
[2]The inspection was performed at 10,000 lux due to the colored solution.

TABLE 6

Summary of the results of optical inspection by stereo-microscopy[3] (molded vials)

| Sample set No. | Scattering[1] | Coloration[2] | Scattering area |
|---|---|---|---|
| 01: RLD vials | I (7/10) 0 (3/10) | 0 (10/10) | Wall near bottom |

TABLE 6-continued

Summary of the results of optical inspection by stereo-microscopy[3] (molded vials)

| Sample set No. | Scattering[1] | Coloration[2] | Scattering area |
|---|---|---|---|
| 01: RLD vials | II (9/10) I (1/10) | 0 (10/10) | Wall near shoulder |

[1]Intensity of the light scattering
[2]Intensity of the coloration
[3]Qualitative classification
0: not observed
I: weak
II: medium
III: strong

TABLE 7

Summary of the results of optical inspection by stereo-microscopy[4] (tubular vials)

| Sample set No. | Scattering[1], area A | Coloration[2], area A/B | Scattering[3], area B |
|---|---|---|---|
| 02: Fortis, empty controls | II (2/5) I (3/5) | I A/0 B (1/5) 0 A/0 B (4/5) | 0 (5/5) |
| 03: Fortis, t0: initial | III (2/10) II (8/10) | 0 (10/10) | II (1/10) I (9/10) |
| 04: Fortis, t1: 5 weeks, 60° C. | III (5/10) II (5/10) | I A/0 B (3/10) 0 A/I B (2/10) 0 A/0 B (5/10) | III (2/10) II (7/10) I (1/10) |
| 05: Fortis, t2: 10 weeks, 60° C. | III (5/10) II (5/10) | I A/III B (1/10) I A/I B (9/10) | II (10/10) |

Figure 9:
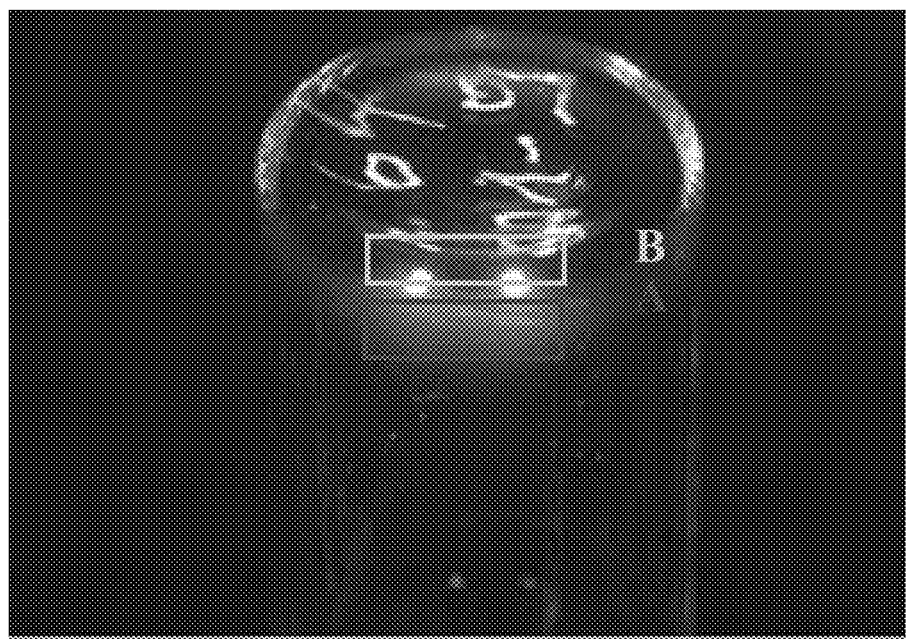
FIG. 9 illustrates visual and optical inspection of a sample vial according to one embodiment of the present disclosure.

[1]Intensity of the light scattering in the circumferential zone A ("white ring"; FIG. 9)
[2]Intensity of the coloration in the circumferential zones A and B (FIG. 9)
[3]Intensity of the light scattering in the circumferential zone B (between "white ring" and bottom; FIG. 9)
[4]Qualitative classification
0: not observed
I: weak
II: medium
III: strong

TABLE 8

Summary of the results of optical inspection by stereo-microscopy[3] (tubular vials)

| Sample set No. | Scattering[1], area C | Coloration[2], area C |
|---|---|---|
| 02: Fortis, empty controls | I (1/5) 0 (4/5) | 0 (5/5) |
| 03: Fortis, t0: initial | I (2/10) 0 (8/10) | 0 (10/10) |

TABLE 8-continued

Summary of the results of optical inspection by stereo-microscopy[3] (tubular vials)

| Sample set No. | Scattering[1], area C | Coloration[2], area C |
|---|---|---|
| 04: Fortis, t1: 5 weeks, 60° C. | 0 (10/10) | 0 (10/10) |
| 05: Fortis, t2: 10 weeks, 60° C. | I (6/10) | 0 (10/10) |
|  | 0 (4/10) |  |

Figure 10:
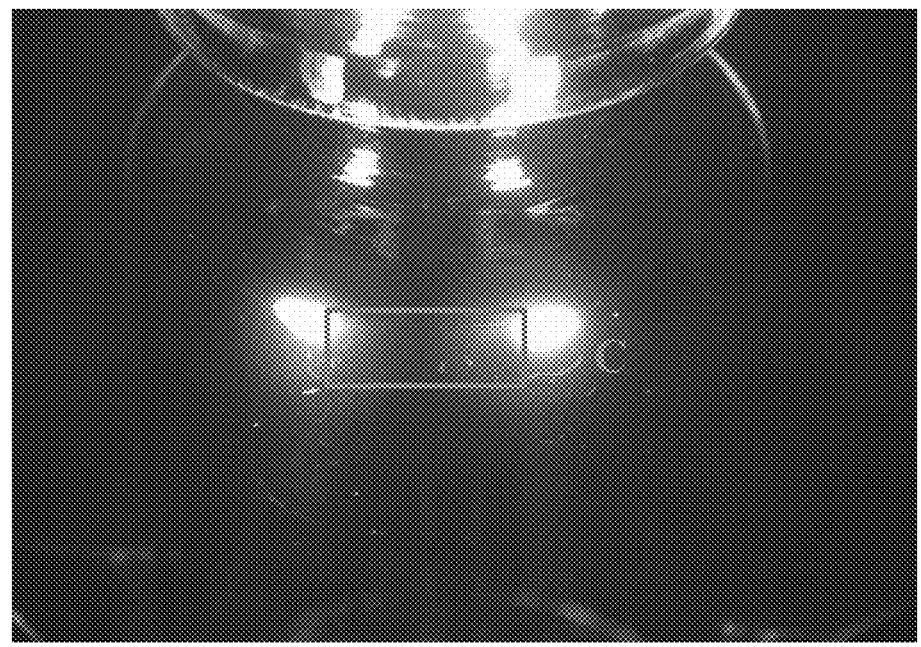
FIG. 10 illustrates visual and optical inspection of a sample vial according to one embodiment of the present disclosure.

[1]Intensity of the light scattering in the circumferential zone C ("shoulder"; FIG. 10)
[2]Intensity of the coloration in the circumferential zone C ("shoulder"; FIG. 10)
[3]Qualitative classification
0: not observed
I: weak
II: medium
III: strong

TABLE 9

Summary of the characteristic features found by SEM analyses[1]

| Sample set No. | Body Wall (near bottom) | Body wall (middle) | Body wall (near shoulder) |
|---|---|---|---|
| 01 (FIGS. 11-12) | Micro-roughness, 2× Deposits (particulate), 2× Shallow pits, 2× | Micro-roughness, 2× Deposits (particulate), 2× | Delaminated areas, 1× Reaction zones, up to about 150 nm*, 2× Micro-roughness, 2× Deposits (particulate), 2× Shallow pits, 2× |
| 02 (FIG. 13) | None | Shallow bumps, 1× Shallow pits, 1× | Micro-roughness, 2× Deposits (particulate), 2× Deposit (planar), 1× Shallow pits, 1× |
| 03 (FIGS. 14-15) | Micro-roughness, 2× Deposits (particulate), 2× Shallow pits, 2× | Micro-roughness, 2× Deposits (particulate), 2× | None |
| 04 (FIGS. 16-17) | Delaminated areas, 2× Reaction zones, up to about 470 nm*, 2× Micro-roughness, 2× Deposits (particulate), 2× Shallow pits, 2× | Deposits (particulate), 2× | Deposits (particulate), 2× Shallow pits, 1× |

[1]A classification is made between 8 characteristic features:
Shallow pits, shallow bumps, micro-roughness, small holes, deposits (particulate), deposits (planar), reaction zones, and delaminated areas.
*Approximate maximum thickness in nm (the thickness is not homogeneous).
Note:
The digit before "x" denotes the number of containers with these features.

TABLE 10

Concentrations of the dissolved "glass" elements (ICP-analyses)

| Element | Al | B | Ca | Si |
|---|---|---|---|---|
| Method | ICP-MS | ICP-OES | ICP-OES | ICP-OES |
| Unit | mg/L | mg/L | mg/L | mg/L |
| 01: RLD vials | <0.05 | 1.5 ± 30% | 0.68 ± 30% | 11 ± 15% |
| 03: Fortis, t0: initial | 0.068 ± 30% | 1.4 ± 30% | 2.3 ± 30% | 9.4 ± 15% |
| 04: Fortis, t1: 5 weeks, 60° C. | 0.070 ± 30% | 2.0 ± 30% | 2.2 ± 30% | 13 ± 15% |
| 06: Matrix solution | <0.05 | <0.5 | 2.1 ± 30% | <0.5 |
| Limit of Quantification | 0.05 | 0.5 | 0.5 | 0.5 |

The relative measurement uncertainties (given in %) were calculated using k = 2.

TABLE 11

Data comparison for chemical composition of sample set 01 (RLD vial) in % [w/w]

| Oxide | Sample 01 | Kimble[1] KG-35 | Bormioli Rocco[2] Type/clear | ASTM E 438[3] Type I, Class B |
|---|---|---|---|---|
| $Al_2O_3$ | 5.43 ± 0.11 | 6 | 5.5 | 7 |
| BaO | 2.23 ± 0.07 | 2 | 2.5 | 0-2 |
| $B_2O_3$ | 11.77 ± 0.20 | 13 | 11.5 | 10 |
| CaO | 1.41 ± 0.03 | 1 | 1 | 1 |
| MgO | <0.05 | 0 | — | <0.3 |
| $K_2O$ | 1.12 ± 0.06 | 1 | 1.5 | 1 |
| $Na_2O$ | 8.0 ± 0.3 | 8 | 7.5 | 6 |
| $SiO_2$ | 69.5 ± 0.5 | 69 | 70.5 | 73 |
| ZnO | 0.022 ± 0.007 | 0 | — | 0.1 |
| $Fe_2O_3$ | 0.046 ± 0.009 | 0 | — | sum <1.0 |
| MnO | 0.041 ± 0.008 | 0 | — |  |
| SrO | 0.041 ± 0.008 | — | — |  |
| $TiO_2$ | <0.02 | 0 | — |  |
| $ZrO_2$ | 0.064 ± 0.013 | — | — |  |

[1]Ibrahim, H., Blundell, R., Gray, M. Device for Packaging an Oxaliplatin Solution, United States Patent Application 2008/0108697.
[2]Bormioli Rocco, Alberto Biavati et al., "Complexing Agents and pH Influence on Chemical Durability of Type 1 Moulded Glass Containers", 2014 PDA Europe Parental Packaging, Mar. 11-12, 2014, Brussles, slide 4.
[3]ASTM E 438-92 - Standard Specifications for Glasses in Laboratory Apparatus.

Example 5—Glass Delamination/Contamination Study of Piramal Molded Vials, Schott Tubular Vials, and Schott Tubular DC Vials Three additional types of vials of the improved anti-delamination featured according to the present disclosure—Piramal Molded Vials, Schott Tubular Vials, and Schott Tubular DC Vials—were tested using the same protocol in Example 4. Similar results were achieved and summarized in "Example 3" of U.S. Provisional Application 63/317,529.

Example 6—Glass Delamination/Contamination Study of Improved Vials

One additional type of vials of the improved anti-delamination featured according to the present disclosure—Fortis 4R—were tested using the same protocol in Example 4. Similar results were achieved and summarized in "Example 4" of U.S. Provisional Application 63/317,529.

What is claimed is:

1. A kit comprising:
an aqueous formulation comprising from about 50 mg/mL to about 300 mg/mL fluorescein sodium, wherein the formulation has a pH of from about 8 to about 10; and
a glass vial holding the aqueous formulation, where the glass vial comprises a shoulder portion that interconnects a neck portion and a body portion, wherein the shoulder portion includes a frustoconical shoulder wall that extends toward the body portion at a transition angle ($\beta$) of at least 120°,
wherein the aqueous formulation has a dissolved silicon concentration upon filling the glass vial ($Si_{0w}$), and a dissolved silicon concentration after storage in the glass vial at 60° C. for 10 weeks ($Si_{10w}$), wherein $Si_{10w}/Si_{0w}$ is from 1 to 1.6;
the aqueous formulation has a dissolved boron concentration upon filing the glass vial ($B_{0w}$), and a dissolved boron concentration after storage in the glass vial at 60° C. for 10 weeks ($B_{10w}$), wherein $B_{10w}/B_{0w}$ is from 1 to 1.9;
$Si_{10w}$ is less than 14 mg/L; and
$B_{10w}$ is less than 2.2 mg/L.

2. The kit of claim 1, wherein $Si_{10w}/Si_{0w}$ is from 1 to 1.4.

3. The kit of claim 1, wherein $B_{10w}/B_{0w}$ is from 1 to 1.6.

4. The kit of claim 1, wherein the glass vial has a bottom reaction zone upon filling the glass vial ($BTRZ_{0w}$) of no more than 20 nm, and the glass vial has a bottom reaction zone after storage in the glass vial at 60° C. for 10 weeks ($BTRZ_{10w}$) of no more than 250 nm.

5. The kit of claim 4, wherein $BTRZ_{10w}$ is no more than 200 nm.

6. The kit of claim 4, wherein $BTRZ_{10w}$ is no more than 150 nm.

7. The kit of claim 4, wherein $BTRZ_{10w}$ is no more than 100 nm.

8. The kit of claim 4, wherein $BTRZ_{10w}$ is no more than 50 nm.

9. The kit of claim 4, wherein $BTRZ_{10w}$ is no more than 10 nm.

10. The kit of claim 4, wherein $BTRZ_{0w}$ is no more than 10 nm.

11. The kit of claim 1, wherein the aqueous formulation comprises from about 70 mg/mL to about 130 mg/mL of fluorescein sodium.

12. The kit of claim 1, wherein the aqueous formulation comprises from about 90 mg/mL to about 110 mg/mL of fluorescein sodium.

13. The kit of claim 1, wherein the aqueous formulation comprises from about 200 mg/mL to about 300 mg/mL of fluorescein sodium.

14. The kit of claim 1, wherein the aqueous formulation comprises from about 230 mg/mL to about 270 mg/mL of fluorescein sodium.

15. The kit of claim 1, wherein the aqueous formulation comprises a pH adjusting agent selected from sodium hydroxide, hydrochloric acid, or a combination thereof.

16. The kit of claim 1, wherein the aqueous formulation is a solution.

17. The kit of claim 1, wherein the glass vial is sealed.

18. The kit of claim 1, wherein the glass vial has a fill volume of from 2 mL to 5 mL.

19. The kit of claim 1, wherein the frustoconical shoulder wall extends toward the neck portion at a transition angle ($\alpha$) of at least 120°.

20. The kit of claim 19, wherein the frustoconical shoulder wall extends toward the body portion at a transition angle ($\beta$) of at least 140°.

21. The kit of claim 20, wherein frustoconical shoulder wall extends toward the neck portion at a transition angle ($\alpha$) of at least 140°.

22. The kit of claim 1, wherein the formulation is suitable for intravenous injection.

23. The kit of claim 1, wherein the formulation is suitable for diagnosis of an ophthalmic disease or condition.

* * * * *

UNITED STATES PATENT AND TRADEMARK OFFICE
CERTIFICATE OF CORRECTION

| | |
|---|---|
| PATENT NO. | : 11,793,891 B2 |
| APPLICATION NO. | : 18/118723 |
| DATED | : October 24, 2023 |
| INVENTOR(S) | : Patrick H. Witham et al. |

It is certified that error appears in the above-identified patent and that said Letters Patent is hereby corrected as shown below:

On the Title Page

In Column 2, Item (57), under "ABSTRACT", delete:
"Compositions comprising a fluorescein component and benoxinate component and the corresponding uses of these compositions are described herein. These compositions have improved storage life and the fluorescein component and/or benoxinate component minimally degrade after 12 to 18 months of storage."

And insert:
-- Provided herein are kits for fluorescein or fluorescein sodium that have reduced amount of delamination or glass attack on the vial, and/or the resulting delaminated glass impurities in the formulation. In some embodiment, the kit has reduced amount of delamination or glass attack on the vial, and/or the resulting delaminated glass impurities in the formulation after storage conditions, e.g. 10 weeks of storage at about 60° C. --

Signed and Sealed this
Ninth Day of July, 2024

Katherine Kelly Vidal
*Director of the United States Patent and Trademark Office*